United States Patent
Buettelmann et al.

(10) Patent No.: US 9,353,102 B2
(45) Date of Patent: May 31, 2016

(54) NON-ANNULATED THIOPHENYLAMIDES

(71) Applicant: Hoffmann-La Roche Inc., Little Falls, NJ (US)

(72) Inventors: Bernd Buettelmann, Schopfheim (DE); Simona M. Ceccarelli, Basel (CH); Holger Kuehne, Loerrach (DE); Bernd Kuhn, Reinach (CH); Werner Neidhart, Hagenthal-le-Bas (FR); Ulrike Obst Sander, Reinach (CH); Hans Richter, Grenzach-Wyhlen (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/645,012

(22) Filed: Mar. 11, 2015

(65) Prior Publication Data
US 2015/0183778 A1    Jul. 2, 2015

Related U.S. Application Data

(63) Continuation of application No. PCT/EP2013/068565, filed on Sep. 9, 2013.

(30) Foreign Application Priority Data
Sep. 12, 2012  (EP) .................................. 12184125

(51) Int. Cl.
| C07D 417/04 | (2006.01) |
| C07D 417/14 | (2006.01) |
| C07D 413/04 | (2006.01) |
| C07D 413/14 | (2006.01) |
| C07D 333/36 | (2006.01) |

(52) U.S. Cl.
CPC ............ *C07D 417/14* (2013.01); *C07D 413/04* (2013.01); *C07D 413/14* (2013.01); *C07D 417/04* (2013.01); *C07D 333/36* (2013.01)

(58) Field of Classification Search
CPC .. C07D 417/04; C07D 417/14; C07D 413/04; C07D 413/14
See application file for complete search history.

(56) References Cited

U.S. PATENT DOCUMENTS

2010/0168084 A1    7/2010    Huber et al.

FOREIGN PATENT DOCUMENTS

| WO | WO 2007036730 A1 * | 4/2007 |
| WO | 2007/036730 | 5/2007 |
| WO | 2008/109856 | 12/2008 |

OTHER PUBLICATIONS

Luquet et al. Biochimica et Biophysica Acta 2005, 1740, 313-317.*
CAS Registry Entry for Registry No. 888124-32-1, which entered STN on Jun. 18th, 2006.*
CAS Registry Entry for Registry No. 693218-41-6, which entered STN on Jun. 15th, 2004.*
CAS Registry Entry for Registry No. 491599-28-1, which entered STN on Feb. 18th, 2003.*
Morgan et al. International Journal of Oncology 2008, 32, 767-775.*
Hussain et al. Diabetes Research and Clinical Practice 2007, 76, 317-326.*
Luo et al. Cell, 2009, 136, pp. 823-837.*
CAS Registry Database, 888124-32-1, Jun. 18, 2006.
Elkoholy, "Studies with 2-benzothiazolylacetonitrile, synthesis of new 2-thienylbenzothiazoles and n-thienyl maleimide derivatives" Phos Sulfur & Silicon 177(1):115-122 (Jan. 1, 2002).
Hertzel et al., "Identification and Characterization of a Small Molecule Inhibitor of Fatty Acid Binding Proteins" J Med Chem 52(19) (Oct. 8, 2009).
Ishikawa, "Cyclic Guanidines. XIII. Synthesis of 2-Amino-4-phenyl-3-4-dihydrothieno [2,3-d] pyrimidine Derivatives" ChemPharmBull 28(11):3172-3177 ( 1980).
Qinyuan et al., "Design, synthesis and biological evaluation of thiazole- and indole-based derivatives for the treatment of type II diabetes" Eur J. Med Chem 52:70-81 (Mar. 2, 2012).

* cited by examiner

*Primary Examiner* — Matthew Coughlin

(57) ABSTRACT

The invention provides novel compounds having the general formula (I)

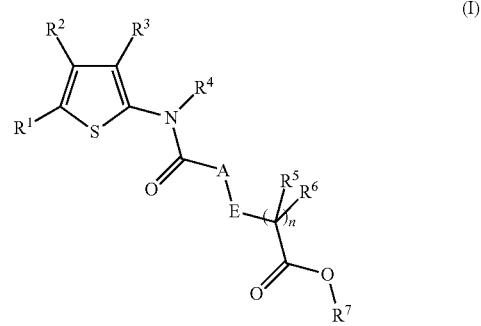

wherein $R^1$, $R^2$, $R^3$, $R^4$, $R^5$, $R^6$, $R^7$, A, E and n are as described herein, compositions including the compounds and methods of using the compounds.

15 Claims, No Drawings

NON-ANNULATED THIOPHENYLAMIDES

This application is a continuation of International Application PCT/EP2013/068565, filed Sep. 9, 2013, which claims the benefit of priority to European Application 12184125.8, filed Sep. 12, 2012, each of which is incorporated herein by reference in its entirety.

The present invention relates to organic compounds useful for therapy or prophylaxis in a mammal, and in particular to fatty-acid binding protein (FABP) 4 and/or 5 inhibitors, more particularly dual FABP 4/5 inhibitors for the treatment or prophylaxis of e.g. type 2 diabetes, atherosclerosis, chronic kidney diseases, non-alcoholic steatohepatitis and cancer.

The present invention provides novel compounds of formula (I)

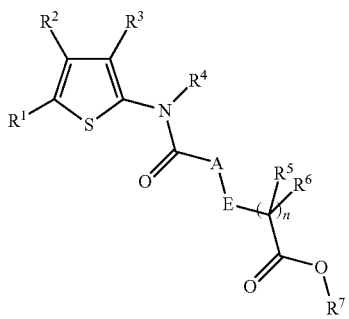

wherein
- $R^1$ and $R^2$ are independently selected from H, alkyl, haloalkyl, alkoxyalkyl, haloalkoxyalkyl, cycloalkyl, cycloalkylalkyl, halocycloalkyl, halocycloalkylalkyl, substituted aryl, substituted arylalkyl, substituted heterocycloalkyl, substituted heterocycloalkylalkyl, substituted heteroaryl, substituted heteroarylalkyl, substituted aminocarbonyl, alkoxycarbonyl, haloalkoxycarbonyl and carboxy, wherein substituted aryl, substituted arylalkyl, substituted heterocycloalkyl, substituted heterocycloalkylalkyl, substituted heteroaryl and substituted heteroarylalkyl are substituted with $R^{14}$, $R^{15}$ and $R^{16}$, and wherein substituted aminocarbonyl is substituted on the nitrogen atom with one to two substituents independently selected from H, alkyl, cycloalkyl, haloalkyl, alkylcycloalkyl, cycloalkylalkyl, alkylcycloalkylalkyl, hydroxyalkyl and alkoxyalkyl;
- $R^3$ is a substituted aryl, substituted arylalkyl, substituted heterocycloalkyl, substituted heterocycloalkylalkyl, substituted heteroaryl or substituted heteroarylalkyl, wherein substituted aryl, substituted arylalkyl, substituted heterocycloalkyl, substituted heterocycloalkylalkyl, substituted heteroaryl and substituted heteroarylalkyl are substituted with $R^{17}$, $R^{18}$ and $R^{19}$;
- $R^4$ is H or alkyl;
- $R^5$ and $R^6$ are independently selected from H, alkyl and cycloalkyl;
- $R^7$ is H, alkyl or cycloalkyl;
- A is $NR^8$ or $CR^9R^{10}$;
- E is $NR^{11}$ or $CR^{12}R^{13}$;
- $R^8$ and $R^{11}$ are independently selected from H, alkyl, haloalkyl, cycloalkyl, halocycloalkyl, cycloalkylalkyl or halocycloalkylalkyl;
- $R^9$, $R^{10}$, $R^{12}$ and $R^{13}$ are independently selected from H, halogen, alkyl, haloalkyl or cycloalkyl;
- or $R^5$ and $R^{12}$ together with the carbon atoms to which they are attached form a substituted cycloalkyl, substituted cycloalkenyl, substituted aryl, substituted heterocycloalkyl or substituted heteroaryl, wherein substituted cycloalkyl, substituted cycloalkenyl, substituted aryl, substituted heterocycloalkyl and substituted heteroaryl are substituted with $R^{20}$ and can be further substituted with $R^{21}$ and/or $R^{22}$, wherein in case $R^5$ and $R^{12}$ together with the carbon atoms to which they are attached form a substituted aryl or substituted heteroaryl, then $R^6$ and $R^{13}$ are absent;
- or $R^8$ and $R^{12}$ together with the nitrogen and carbon atoms to which they are attached form a substituted heterocycloalkyl or substituted heteroaryl, wherein substituted heterocycloalkyl and substituted heteroaryl are substituted with $R^{20}$ and can be further substituted with $R^{21}$ and/or $R^{22}$, wherein in case $R^8$ and $R^{12}$ together with the carbon atoms to which they are attached form a substituted heteroaryl, then $R^{13}$ is absent;
- or $R^9$ and $R^{11}$ together with the nitrogen and carbon atoms to which they are attached form a substituted heterocycloalkyl or substituted heteroaryl, wherein substituted heterocycloalkyl and substituted heteroaryl are substituted with $R^{20}$ and can be further substituted with $R^{21}$ and/or $R^{22}$, wherein in case $R^9$ and $R^{11}$ together with the carbon atoms to which they are attached form a substituted heteroaryl, then $R^{10}$ is absent;
- or $R^9$ and $R^{12}$ together with the carbon atoms to which they are attached form a substituted cycloalkyl, substituted cycloalkenyl, substituted aryl, substituted heterocycloalkyl or substituted heteroaryl, wherein substituted cycloalkyl, substituted cycloalkenyl, substituted aryl, substituted heterocycloalkyl and substituted heteroaryl are substituted with $R^{20}$ and can be further substituted with $R^{21}$ and/or $R^{22}$, wherein in case $R^9$ and $R^{12}$ together with the carbon atoms to which they are attached form a substituted aryl or substituted heteroaryl, then $R^{10}$ and $R^{13}$ are absent;
- or $R^{10}$ and $R^{13}$ together with the carbon atoms to which they are attached form a substituted cycloalkyl, substituted cycloalkenyl, substituted aryl, substituted heterocycloalkyl or substituted heteroaryl, wherein substituted cycloalkyl, substituted cycloalkenyl, substituted aryl, substituted heterocycloalkyl and substituted heteroaryl are substituted with $R^{23}$ and can be further substituted with $R^{24}$ and/or $R^{25}$, wherein in case $R^{10}$ and $R^{13}$ together with the carbon atoms to which they are attached form a substituted aryl or substituted heteroaryl, then $R^9$ and $R^{12}$ are absent;
- or $R^{10}$ and $R^{13}$ together with the carbon atoms to which they are attached form a double bond;
- $R^{14}$, $R^{15}$, $R^{16}$, $R^{17}$, $R^{18}$, $R^{19}$, $R^{20}$, $R^{21}$, $R^{23}$, $R^{24}$ and $R^{25}$ are independently selected from H, hydroxy, oxo, halogen, alkyl, haloalkyl, cycloalkyl, halocycloalkyl, alkoxy, haloalkoxy, alkoxyalkyl, haloalkoxyalkyl, alkoxycarbonyl, carboxy and amino substituted on the nitrogen atom with one to two substituents independently selected from H alkyl, cycloalkyl, haloalkyl, alkylcycloalkyl, cycloalkylalkyl, alkylcycloalkylalkyl, hydroxyalkyl and alkoxyalkyl;
- n is zero or 1;
- or pharmaceutically acceptable salts.

FABP4 (aP2) and FABP5 (mal1) are members of the fatty acid binding protein family. FABPs are proteins of 14-15 KDa that act as chaperones for fatty acids in the aqueous cytosolic environment and facilitate their movement between cellular compartments. So far at least nine members of this family have been identified with a tissue-specific pattern of expression. FABP4 is mainly expressed in adipose and macrophages, but also in other cell types, whereas FABP5 is expressed in a wide range of tissues and organs. FABPs are responsible for the transfer of fatty acids to different cell compartments and are thus implicated in key cellular functions such as lipid storage in adipocytes, fatty acid oxidation in mitochondria, ER signaling, fatty-acid-dependent gene expression, regulation of cytosolic enzymes activity, modulation of inflammatory response and leukotrienes synthesis. Plasma FABP4 is secreted by adipose tissue in mice and secretion is de-regulated in obesity and blocking of plasma FABP4 in vivo by antibodies improves insulin sensitivity.

Several genetic evidences in human support a role of FABP4 and FABP5 in metabolic diseases. A mutation in the FABP4 promoter (SNP T-87C) leading to 50% reduction in gene expression is associated to reduced cardiovascular diseases (CVDs) and type 2 diabetes (T2D) risk and to reduced plasma triglycerides (TGs). Two mutations in FABP5 gene, one in the 5'UTR (rs454550), one in the promoter (nSNP), are associated, respectively to increased (OR 4.24) and decreased risk (OR 0.48) of T2D. In addition, it was shown that FABP4 protein and mRNA levels in atherosclerotic plaque macrophages are associated to plaques instability and CV death. Finally, a large number of publications report an association between FABP4 and FABP5 plasma levels and severity of metabolic diseases. Elevated FABP4 plasma levels are associated with atherogenic dyslipidemia, reduced endothelial function, increased intima-media (IM) thickness, metabolic syndrome, obesity and insulin resistance IR. Elevated FABP5 plasma levels are associated to metabolic syndrome.

Genetic and pharmacological studies in mice largely confirm the human evidences. It was demonstrated that loss-of-function in FABP4 and FABP5 improves insulin sensitivity, lowers glucose, and protects against atherosclerosis. FABP4 knockout mice on high fat diet showed metabolic improvement that was tempered by compensatory upregulation of FABP5 in adipose. Mice with a deletion of FABP5 gene on high fat (HF) diet showed body weight reduction and improved glucose and insulin tolerance. The FABP4/FABP5 double-knockout mice were strongly protected from hyperglycemia, insulin resistance, and hepatic steatosis. In addition, in an ApoE deficient background, FABP4 and FABP5 deletion was highly protective against the development of atherosclerosis and increased longevity. A specific FABP4 inhibitor (BMS309403), showed in a clamp study in ob/ob mice a reduction of hepatic glucose production, increased glucose uptake in muscle and adipose and reduction in hepatic steatosis, but no change in body weight and energy consumption. Also, it showed a decrease in atherosclerotic placques formation in ApoE KO mice. A dual FABP4/5 inhibitor Compound 3 described in J. Lipid Res. 2011, 52, 646 showed in mice under HF diet a reduction in plasma triglyceride and free fatty acid, but no improvement in insulin and glucose tolerance.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of type 2 diabetes, metabolic syndrome, atherosclerosis, dyslipidemia, liver diseases involving inflammation, steatosis and/or fibrosis, such as non-alcoholic fatty liver disease, in particular non-alcoholic steatohepatitis, obesity, lipodystrophy, such as genetic and iatrogenic lipodystrophy, cancer, eye diseases supported by endothelial proliferation and angiogenesis, such as macular degeneration and retinopathy, lung diseases, such as asthma, bronchopulmonary dysplasia and chronic obstructive pulmonary disease, sarcoidosis, chronic renal diseases, such as vasculitis, focal segmental glomerulosclerosis, diabetic nephropathy, lupus nephritis, polycystic kidney disease and drug or toxin-induced chronic tubulointerstitial nephritis, chronic inflammatory and autoimmune inflammatory diseases, preeclampsia and polycystic ovary syndrome, and the use of the said compounds, salts or esters for the production of medicaments for the treatment or prophylaxis of of type 2 diabetes, metabolic syndrome, atherosclerosis, dyslipidemia, liver diseases involving inflammation, steatosis and/or fibrosis, such as non-alcoholic fatty liver disease, in particular non-alcoholic steatohepatitis, obesity, lipodystrophy, such as genetic and iatrogenic lipodystrophy, cancer, eye diseases supported by endothelial proliferation and angiogenesis, such as macular degeneration and retinopathy, lung diseases, such as asthma, bronchopulmonary dysplasia and chronic obstructive pulmonary disease, sarcoidosis, chronic renal diseases, such as vasculitis, focal segmental glomerulosclerosis, diabetic nephropathy, lupus nephritis, polycystic kidney disease and drug or toxin-induced chronic tubulointerstitial nephritis, chronic inflammatory and autoimmune inflammatory diseases, preeclampsia and polycystic ovary syndrome.

Compounds of the present invention are FABP 4 and/or 5 inhibitors, more particularly dual FABP 4 and 5 inhibitors. Some particular compounds of formula (I) of the present invention are also selective FABP 4 and/or 5 inhibitors compared to FABP 3 and/or 1.

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy, ethoxy and isopropoxy. A more particular alkoxy group is methoxy.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl and ethoxypropyl.

Particular alkoxyalkyl group include methoxymethyl and methoxyethyl. A more particular alkoxyalkyl group is methoxyethyl.

The term "alkoxycarbonyl" denotes a group of the formula —C(O)—R', wherein R' is an alkoxy group. Examples of alkoxycarbonyl group include group wherein R' is methoxy, ethoxycarbonyl, n-propoxycarbonyl, isopropoxy, n-butoxy, isobutoxy and tert-butoxy. Particular alkoxycarbonyl groups include groups wherein R' is methoxy, ethoxy, isopropoxy and tert-butoxy. In more particular alkoxycarbonyl groups R' is methoxy or ethoxy.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, and tert-butyl. Particular alkyl is methyl.

The term "alkylcycloalkyl" denotes a cycloalkyl group wherein at least one of the hydrogen atoms of the cycloalkyl group has been replaced an alkyl group. Examples of alkylcycloalkyl include methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular alkylcycloalkyl groups include methyl-cyclopropyl and dimethyl-cyclopropyl.

The term "alkylcycloalkylalkyl" denotes an alkyl group wherein at least one of the hydrogen atoms of the alkyl group is replaced by an alkylcycloalkyl group. Examples of alkylcycloalkylalkyl include methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "amino" denotes a —NH$_2$ group.

The term "aminocarbonyl" denotes a group of the formula —C(O)—NH$_2$.

The term "aryl" denotes a monovalent aromatic carbocyclic mono- or bicyclic ring system comprising 6 to 10 carbon ring atoms. Examples of aryl moieties include phenyl and naphthyl. Particular aryl group is phenyl.

The term "arylalkyl" denotes an alkyl group wherein at least one of the hydrogen atoms of the alkyl group has been replaced by an aryl group. Examples of arylalkyl include phenylmethyl and phenylethyl.

The term "carbonyl" denotes a —C(O)— group.

The term "carboxy" denotes a —C(O)OH group.

The term "cycloalkenyl" denotes a monovalent unsaturated non-aromatic monocyclic or bicyclic hydrocarbon group of 3 to 8 ring carbon atoms. Particular cycloalkenyl groups are monocyclic. Examples of cycloalkenyl groups include cyclobutenyl, cyclopentenyl and cyclohexenyl.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated or partially saturated carbocycles having two carbon atoms in common. Particular cycloalkyl groups are cyclopropyl, cyclobutyl, cyclopentyl, cyclohexyl, cycloheptanyl, bicyclo[2.2.2]heptanyl, bicyclo[2.2.2]octanyl, substituted bicyclo[2.2.2]heptanyl and substituted bicyclo[2.2.2]octanyl.

In the case of R$^1$, R$^2$, R$^{17}$, R$^{18}$ and R$^{19}$, particular example of cycloalkyl is cyclopropyl.

In the case of the cycloalkyl formed by R$^9$ and R$^{12}$ together with the carbon atoms to which they are attached, particular examples of cycloalkyl are cyclopentyl, cyclohexyl and bicyclo[2.2.2]octanyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy, trifluoroethoxy and trifluoromethylethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl. Particular haloalkoxyalkyl is 2,2-difluoroethoxyethyl.

The term "haloalkoxycarbonyl" denotes a group of the formula —C(O)—R', wherein R' is an haloalkoxy group. Examples of haloalkoxycarbonyl groups include a group of the formula —C(O)—R', wherein R' is fluoromethoxy, difluoromethoxy, trifluoromethoxy, trifluoroethoxy, trifluoromethylethoxy, trifluorodimethylethoxy or pentafluoroethoxy.

The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl and trifluoroethyl.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl groups include fluorocyclopropyl, difluorocyclopropyl, fluorocyclobutyl and difluorocyclobutyl.

The term "halocycloalkylalkyl" denotes an alkyl group wherein at least one of the hydrogen atoms of the alkyl group has been replaced by a halocycloalkyl. Examples of halocycloalkylalkyl groups include fluorocyclopropylmethyl, fluorocyclopropylethyl, difluorocyclopropylmethyl, difluorocyclopropylethyl, fluorocyclobutylmethyl, fluorocyclobutylethyl, difluorocyclobutylmethyl and difluorocyclobutylethyl.

The term "halogen" and "halo" are used interchangeably herein and denote fluoro, chloro, bromo, or iodo. Particular halogens are chloro and fluoro. More particular halogen is fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzisoxazolyl, benzothiazolyl, benzisothiazolyl, benzoxadiazolyl, benzothiadiazolyl, benzotriazolyl, purinyl, quinolinyl, isoquinolinyl, quinazolinyl, or quinoxalinyl. Particular heteroaryl groups are oxadiazolyl, oxazolyl, thiazolyl, thiadiazolyl, pyridinyl or pyrimidinyl. Further particular heteroaryl groups are [1,2,4]-oxadiazolyl, thiazolyl and thiadiazolyl.

In the case of R$^1$ and R$^2$, particular heteroaryl group is thiadiazolyl.

In the case of R$^3$ particular heteroaryl groups are thiazolyl, [1,2,4]-thiadiazolyl and [1,2,4]-oxadiazolyl.

The term "heteroarylalkyl" denotes an alkyl group wherein at least one of the hydrogen atoms of the alkyl group has been replaced by a heteroaryl group.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Further particular example of heterocycloalkyl group is oxetanyl.

The term "heterocycloalkylalkyl" denotes an alkyl group wherein at least one of the hydrogen atoms of the alkyl group has been replaced by a heterocycloalkyl group.

The term "hydroxy" denotes a —OH group.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl. Particular examples are hydroxymethyl and hydroxyethyl.

The term "oxo" denotes a =O group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts. Particular pharmaceutically acceptable salts of compounds of formula (I) are also the sodium and potassium salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A further embodiment of the present invention are compounds according to formula (I) as described herein, wherein $R^1$ and $R^2$ are independently selected from H, alkyl, haloalkyl, cycloalkyl, substituted heterocycloalkyl, substituted heteroaryl, substituted aminocarbonyl and alkoxycarbonyl, wherein substituted heterocycloalkyl and substituted heteroaryl are substituted with $R^{14}$, $R^{15}$ and $R^{16}$, and wherein substituted aminocarbonyl is substituted on the nitrogen atom with one to two substituents independently selected from H, alkyl, cycloalkyl, haloalkyl, alkylcycloalkyl, cycloalkylalkyl, alkylcycloalkylalkyl, hydroxyalkyl and alkoxyalkyl.

A particular embodiment of the present invention are compounds according to formula (I) as described herein, wherein $R^1$ and $R^2$ are independently selected from H, alkyl, haloalkyl, cycloalkyl, substituted heterocycloalkyl, substituted heteroaryl, substituted aminocarbonyl and alkoxycarbonyl, wherein substituted heterocycloalkyl and substituted heteroaryl are substituted with $R^{14}$, $R^{15}$ and $R^{16}$, and wherein substituted aminocarbonyl is substituted on the nitrogen atom with two substituents independently selected alkyl.

A particular embodiment of the present invention are compounds according to formula (I) as described herein, wherein $R^1$ is H, alkyl, haloalkyl, cycloalkyl, substituted heterocycloalkyl, substituted heteroaryl, substituted aminocarbonyl and alkoxycarbonyl, wherein substituted heterocycloalkyl and substituted heteroaryl are substituted with $R^{14}$, $R^{15}$ and $R^{16}$, and wherein substituted aminocarbonyl is substituted on the nitrogen atom with two substituents independently selected from H, alkyl, cycloalkyl, haloalkyl, alkylcycloalkyl, cycloalkylalkyl, alkylcycloalkylalkyl, hydroxyalkyl and alkoxyalkyl.

In a further embodiment of the present invention are compounds according to formula (I) as described herein, wherein $R^1$ is alkyl or cycloalkyl.

Another further embodiment of the present invention are compounds according to formula (I) as described herein, wherein $R^2$ is H, alkyl, haloalkyl or cycloalkyl.

Another embodiment of the present invention are compounds according to formula (I) as described herein, wherein $R^2$ is alkyl or haloalkyl.

Another particular embodiment of the present invention are compounds according to formula (I) as described herein, wherein $R^1$ and $R^2$ are independently selected from H, alkyl or cycloalkyl.

The present invention also relates to compounds according to formula (I) as described herein, wherein $R^1$ and $R^2$ are alkyl.

A further particular embodiment of the present invention are compounds according to formula (I) as described herein, wherein $R^3$ is a substituted aryl or substituted heteroaryl, wherein substituted aryl and substituted heteroaryl are substituted with $R^{17}$, $R^{18}$ and $R^{19}$.

A more particular embodiment of the present invention are compounds according to formula (I) as described herein, wherein $R^3$ is heteroaryl substituted with $R^{17}$, $R^{18}$ and $R^{19}$.

Also an embodiment of the present invention are compounds according to formula (I) as described herein, wherein $R^3$ is pyrrolidinyl, substituted [1,2,4]-oxadiazolyl, oxazolyl, substituted thiazolyl, substituted [1,2,4]thiadiazol-5-yl, or pyrimidinyl, wherein substituted [1,2,4]-oxadiazolyl, substituted [1,2,4]thiadiazol-5-yl and substituted thiazolyl are substituted with $R^{17}$.

Also an embodiment of the present invention are compounds according to formula (I) as described herein, wherein $R^3$ is pyrrolidinyl, substituted [1,2,4]-oxadiazolyl, oxazolyl, substituted thiazolyl or pyrimidinyl, wherein substituted [1,2,4]-oxadiazolyl and substituted thiazolyl are substituted with $R^{17}$.

The present invention also relates to compounds according to formula (I) as described herein, wherein $R^3$ is substituted [1,2,4]-oxadiazolyl or substituted [1,2,4]thiadiazol-5-yl, wherein substituted [1,2,4]-oxadiazolyl and substituted [1,2,4]thiadiazol-5-yl are substituted with $R^{17}$.

Another embodiment of the present invention are compounds according to formula (I) as described herein, wherein $R^3$ is [1,2,4]-oxadiazolyl substituted with $R^{17}$.

A further particular embodiment of the present invention are compounds according to formula (I) as described herein, wherein is $R^4$ is H.

A particular embodiment of the present invention are compounds according to formula (I) as described herein, wherein $R^7$ is H.

Also an embodiment of the present invention are compounds according to formula (I) as described herein, wherein A is $CR^9R^{10}$.

A further particular embodiment of the present invention are compounds according to formula (I) as described herein, wherein E is $CR^{12}R^{13}$.

A further particular embodiment of the present invention are compounds according to formula (I) as described herein, wherein in case A is $NR^8$, then E is $CR^{12}R^{13}$.

A further particular embodiment of the present invention are compounds according to formula (I) as described herein, wherein in case E is $NR^{11}$, then A is $CR^9R^{10}$.

The present invention also relates to compounds according to formula (I) as described herein, wherein $R^9$ and $R^{12}$ together with the carbon atoms to which they are attached form a substituted cycloalkyl, substituted cycloalkenyl, substituted aryl, substituted heterocycloalkyl or substituted heteroaryl, wherein substituted cycloalkyl, substituted cycloalkenyl, substituted aryl, substituted heterocycloalkyl and substituted heteroaryl are substituted with $R^{20}$ and can be further substituted with $R^{21}$ and/or $R^{22}$, wherein in case $R^9$ and $R^{12}$ together with the carbon atoms to which they are attached form a substituted aryl or substituted heteroaryl, then $R^{10}$ and $R^{13}$ are absent.

Another embodiment of the present invention are compounds according to formula (I) as described herein, wherein $R^9$ and $R^{12}$ together with the carbon atoms to which they are attached form a cycloalkyl substituted with $R^{20}$.

Another embodiment of the present invention are compounds according to formula (I) as described herein, wherein $R^9$ and $R^{12}$ together with the carbon atoms to which they are attached form cyclopentyl, cyclohexyl or bicyclo[2.2.2]octyl.

The present invention also relates to compounds according to formula (I) as described herein, wherein $R^9$ and $R^{12}$ together with the carbon atoms to which they are attached form cyclopentyl or cyclohexyl.

Also an embodiment of the present invention are compounds according to formula (I) as described herein, wherein $R^{10}$ and $R^{13}$ together with the carbon atoms to which they are attached form a double bond.

Also an embodiment of the present invention are compounds according to formula (I) as described herein, wherein $R^{14}$, $R^{15}$, $R^{16}$, $R^{17}$, $R^{18}$, $R^{19}$, $R^{20}$, $R^{21}$, $R^{23}$, $R^{24}$ and $R^{25}$ are independently selected from H, alkyl, haloalkyl and cycloalkyl.

Another embodiment of the present invention are compounds according to formula (I) as described herein, wherein $R^{14}$ is cycloalkyl.

A particular embodiment of the present invention are compounds according to formula (I) as described herein, wherein $R^{17}$ is H, alkyl, haloalkyl or cycloalkyl.

Another particular embodiment of the present invention are compounds according to formula (I) as described herein, wherein $R^{17}$ is alkyl or cycloalkyl.

A further particular embodiment of the present invention are compounds according to formula (I) as described herein, wherein $R^{17}$ is cycloalkyl.

A more particular embodiment of the present invention are compounds according to formula (I) as described herein, wherein $R^{18}$, $R^{19}$, $R^{20}$, $R^{21}$ and $R^{23}$ are H.

Also a particular embodiment of the present invention are compounds according to formula (I) as described herein, wherein n is zero or 1.

In a further particular embodiment of the present invention are compounds according to formula (I) as described herein, wherein $R^1$ and $R^2$ are independently selected from H, alkyl, haloalkyl and cycloalkyl;
$R^3$ is a heteroaryl substituted with $R^{17}$;
$R^4$ is H;
$R^7$ is H;
A is $CR^9R^{10}$;
E is $CR^{12}R^{13}$;
$R^9$ and $R^{12}$ together with the carbon atoms to which they are attached form a cycloalkyl, substituted with $R^{20}$;
$R^{10}$ and $R^{13}$ together with the carbon atoms to which they are attached form a double bond;
$R^{17}$ is H, alkyl, haloalkyl or cycloalkyl;
$R^{20}$ is H;
n is zero;
or pharmaceutically acceptable salts.

Particular examples of compounds of formula (I) as described herein are selected from 2-(3-Phenyl-thiophen-2-ylcarbamoyl)-cyclopent-1-enecarboxylic acid;
5-[(3-Carboxy-bicyclo[2.2.2]oct-2-ene-2-carbonyl)-amino]-3-methyl-4-(4-methyl-thiazol-2-yl)-thiophene-2-carboxylic acid methyl ester;
2-[4-Cyclopropyl-5-methyl-3-(3-methyl-[1,2,4]oxadiazol-5-yl)-thiophen-2-ylcarbamoyl]-cyclopent-1-enecarboxylic acid;
3-[4-Cyclopropyl-5-methyl-3-(3-trifluoromethyl-[1,2,4]oxadiazol-5-yl)-thiophen-2-ylcarbamoyl]-bicyclo[2.2.2]oct-2-ene-2-carboxylic acid;
2-[3-(3-Cyclopropyl-[1,2,4]oxadiazol-5-yl)-4,5-dimethyl-thiophen-2-ylcarbamoyl]-cyclohex-1-enecarboxylic acid;
2-[5-Cyclopropyl-3-(3-cyclopropyl-[1,2,4]oxadiazol-5-yl)-4-methyl-thiophen-2-ylcarbamoyl]-cyclopent-1-enecarboxylic acid;
3-[5-Cyclopropyl-3-(3-cyclopropyl-[1,2,4]oxadiazol-5-yl)-4-methyl-thiophen-2-ylcarbamoyl]-bicyclo[2.2.2]oct-2-ene-2-carboxylic acid;
2-[4-Cyclopropyl-5-methyl-3-(3-methyl-[1,2,4]oxadiazol-5-yl)-thiophen-2-ylcarbamoyl]-cyclohex-1-enecarboxylic acid;
3-[4-Cyclopropyl-5-methyl-3-(3-methyl-[1,2,4]oxadiazol-5-yl)-thiophen-2-ylcarbamoyl]-bicyclo[2.2.2]oct-2-ene-2-carboxylic acid;
2-[4-Cyclopropyl-3-(3-cyclopropyl-[1,2,4]oxadiazol-5-yl)-5-methyl-thiophen-2-ylcarbamoyl]-cyclopent-1-enecarboxylic acid;
3-[4-Cyclopropyl-3-(3-cyclopropyl-[1,2,4]oxadiazol-5-yl)-5-methyl-thiophen-2-ylcarbamoyl]-bicyclo[2.2.2]oct-2-ene-2-carboxylic acid;
3-[3-(3-Cyclopropyl-[1,2,4]oxadiazol-5-yl)-4,5-dimethyl-thiophen-2-ylcarbamoyl]-bicyclo[2.2.2]oct-2-ene-2-carboxylic acid;
2-[3-(3-Cyclopropyl-[1,2,4]oxadiazol-5-yl)-4,5-dimethyl-thiophen-2-ylcarbamoyl]-cyclopent-1-enecarboxylic acid;
2-[4-Cyclopropyl-5-methyl-3-(3-trifluoromethyl-[1,2,4]oxadiazol-5-yl)-thiophen-2-ylcarbamoyl]-cyclopent-1-enecarboxylic acid;
2-[3-(3-Cyclopropyl-[1,2,4]oxadiazol-5-yl)-5-methyl-thiophen-2-ylcarbamoyl]-cyclopent-1-enecarboxylic acid;
2-[3-(3-Cyclopropyl-[1,2,4]oxadiazol-5-yl)-thiophen-2-ylcarbamoyl]-cyclopent-1-enecarboxylic acid;
2-[3-(3-Cyclopropyl-[1,2,4]oxadiazol-5-yl)-4-methyl-5-oxetan-3-yl-thiophen-2-ylcarbamoyl]-cyclopent-1-enecarboxylic acid;
2-[3-(3-Cyclopropyl-[1,2,4]oxadiazol-5-yl)-4-methyl-5-oxetan-3-yl-thiophen-2-ylcarbamoyl]-cyclohex-1-enecarboxylic acid;
2-[3-(3-Cyclopropyl-[1,2,4]oxadiazol-5-yl)-5-methyl-4-trifluoromethyl-thiophen-2-ylcarbamoyl]-cyclopent-1-enecarboxylic acid;
5-[(2-Carboxy-cyclopent-1-enecarbonyl)-amino]-4-(3-cyclopropyl-[1,2,4]oxadiazol-5-yl)-3-methyl-thiophene-2-carboxylic acid ethyl ester;
2-[3-(3-Cyclopropyl-[1,2,4]oxadiazol-5-yl)-5-dimethylcarbamoyl-4-methyl-thiophen-2-ylcarbamoyl]-cyclopent-1-enecarboxylic acid;
2-[5-Cyclopropyl-3-(3-cyclopropyl-[1,2,4]oxadiazol-5-yl)-thiophen-2-ylcarbamoyl]-cyclopent-1-enecarboxylic acid;
2-[4-Cyclopropyl-3-(3-cyclopropyl-[1,2,4]oxadiazol-5-yl)-thiophen-2-ylcarbamoyl]-cyclopent-1-enecarboxylic acid;
2-[3-(3-Cyclopropyl-[1,2,4]oxadiazol-5-yl)-4-methyl-thiophen-2-ylcarbamoyl]-cyclopent-1-enecarboxylic acid;
2-[3-(3-Cyclopropyl-[1,2,4]oxadiazol-5-yl)-5-(2,2,2-trifluoro-ethyl)-thiophen-2-ylcarbamoyl]-cyclopent-1-enecarboxylic acid;
2-[3-(3-Cyclopropyl-[1,2,4]oxadiazol-5-yl)-4-trifluoromethyl-thiophen-2-ylcarbamoyl]-cyclopent-1-enecarboxylic acid;
2-[3-(3-Cyclopropyl-[1,2,4]oxadiazol-5-yl)-5-(5-dimethylamino-[1,2,4]thiadiazol-3-yl)-4-methyl-thiophen-2-ylcarbamoyl]-cyclopent-1-enecarboxylic acid;
and pharmaceutically acceptable salts thereof.

Also particular examples of compounds of formula (I) as described herein are selected from
3-[4,5-Dimethyl-3-(3-methyl-[1,2,4]thiadiazol-5-yl)-thiophen-2-ylcarbamoyl]-bicyclo[2.2.2]oct-2-ene-2-carboxylic acid;
2-[3-(3-Cyclopropyl-[1,2,4]thiadiazol-5-yl)-4,5-dimethyl-thiophen-2-ylcarbamoyl]-cyclopent-1-enecarboxylic acid;
2-[3-(3-Cyclopropyl-[1,2,4]thiadiazol-5-yl)-4,5-dimethyl-thiophen-2-ylcarbamoyl]-cyclohex-1-enecarboxylic acid;
3-[3-(3-Cyclopropyl-[1,2,4]thiadiazol-5-yl)-4,5-dimethyl-thiophen-2-ylcarbamoyl]-bicyclo[2.2.2]oct-2-ene-2-carboxylic acid;
2-[5-Cyclopropyl-4-methyl-3-(3-methyl-[1,2,4]thiadiazol-5-yl)-thiophen-2-ylcarbamoyl]-cyclopent-1-enecarboxylic acid;
2-[5-Cyclopropyl-4-methyl-3-(3-methyl-[1,2,4]thiadiazol-5-yl)-thiophen-2-ylcarbamoyl]-cyclohex-1-enecarboxylic acid;
3-[5-Cyclopropyl-4-methyl-3-(3-methyl-[1,2,4]thiadiazol-5-yl)-thiophen-2-ylcarbamoyl]-bicyclo[2.2.2]oct-2-ene-2-carboxylic acid;
2-[5-Cyclopropyl-3-(3-cyclopropyl-[1,2,4]thiadiazol-5-yl)-4-methyl-thiophen-2-ylcarbamoyl]-cyclopent-1-enecarboxylic acid;
2-[4,5-Dimethyl-3-(3-methyl-[1,2,4]thiadiazol-5-yl)-thiophen-2-ylcarbamoyl]-cyclopent-1-enecarboxylic acid;
3-[5-Cyclopropyl-3-(3-cyclopropyl-[1,2,4]thiadiazol-5-yl)-4-methyl-thiophen-2-ylcarbamoyl]-bicyclo[2.2.2]oct-2-ene-2-carboxylic acid;
(1SR,2SR)-2-[3-(3-Cyclopropyl-[1,2,4]oxadiazol-5-yl)-4,5-dimethyl-thiophen-2-ylcarbamoyl]-cyclohexanecarboxylic acid;
(1RS,2SR)-2-[3-(3-Cyclopropyl-[1,2,4]oxadiazol-5-yl)-4,5-dimethyl-thiophen-2-ylcarbamoyl]-cyclohexanecarboxylic acid;
2-[4,5-Dimethyl-3-(3-methyl-[1,2,4]thiadiazol-5-yl)-thiophen-2-ylcarbamoyl]-cyclohex-1-enecarboxylic acid;
2-[5-Cyclopropyl-3-(3-cyclopropyl-[1,2,4]thiadiazol-5-yl)-4-methyl-thiophen-2-ylcarbamoyl]-cyclohex-1-enecarboxylic acid;
5-[3-(3-Cyclopropyl-[1,2,4]oxadiazol-5-yl)-4,5-dimethyl-thiophen-2-ylcarbamoyl]-3,6-dihydro-2H-pyran-4-carboxylic acid;
4-[3-(3-Cyclopropyl-[1,2,4]oxadiazol-5-yl)-4,5-dimethyl-thiophen-2-ylcarbamoyl]-5,6-dihydro-2H-pyran-3-carboxylic acid;
(R)-1-[4,5-Dimethyl-3-(3-trifluoromethyl-[1,2,4]oxadiazol-5-yl)-thiophen-2-ylcarbamoyl]-pyrrolidine-2-carboxylic acid;
and pharmaceutically acceptable salts thereof.

Further particular examples of compounds of formula (I) as described herein are selected from 2-[3-(3-Cyclopropyl-[1,2,4]oxadiazol-5-yl)-4,5-dimethyl-thiophen-2-ylcarbamoyl]-cyclohex-1-enecarboxylic acid;

2-[5-Cyclopropyl-3-(3-cyclopropyl-[1,2,4]oxadiazol-5-yl)-4-methyl-thiophen-2-ylcarbamoyl]-cyclopent-1-enecarboxylic acid;

2-[3-(3-Cyclopropyl-[1,2,4]oxadiazol-5-yl)-5-methyl-4-trifluoromethyl-thiophen-2-ylcarbamoyl]-cyclopent-1-enecarboxylic acid;

2-[4,5-Dimethyl-3-(3-methyl-[1,2,4]thiadiazol-5-yl)-thiophen-2-ylcarbamoyl]-cyclohex-1-enecarboxylic acid; and pharmaceutically acceptable salts thereof.

Also further particular examples of compounds of formula (I) as described herein are selected from 2-[3-(3-Cyclopropyl-[1,2,4]oxadiazol-5-yl)-4,5-dimethyl-thiophen-2-ylcarbamoyl]-cyclohex-1-enecarboxylic acid;

2-[5-Cyclopropyl-3-(3-cyclopropyl-[1,2,4]oxadiazol-5-yl)-4-methyl-thiophen-2-ylcarbamoyl]-cyclopent-1-enecarboxylic acid;

2-[3-(3-Cyclopropyl-[1,2,4]oxadiazol-5-yl)-5-methyl-4-trifluoromethyl-thiophen-2-ylcarbamoyl]-cyclopent-1-enecarboxylic acid;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the person skilled in the art such as, e.g. chiral chromatography or crystallization. In case one of the starting materials or compounds of formula (I) contain one or more functional groups which are not stable or are reactive under the reaction conditions of one or more reaction steps, appropriate protecting groups can be introduced before the critical step applying methods well known in the art. Such protecting groups can be removed at a later stage of the synthesis using standard methods described in the literature. The substituents and indices used in the following description of the processes have the significance given herein.

The following abbreviations are used in the present text:

AcCl=Acetyl chloride, tert-BuOH=tert-butyl alcohol, CDI=N,N'-carbonyldiimidazole, CHCl$_3$=chloroform, CH$_2$Cl$_2$=dichloromethane, CH$_3$CN=acetonitrile, Cs$_2$CO$_3$=cesium carbonate, DBU=1,8-diazabicyclo[5.4.0]undec-7-ene, DCC=N,N'-dicyclohexylcarbodiimide, DIPEA=diisopropylethylamine (Huenig's base), DMAP=4-dimethylaminopyridine, DMA=N,N-dimethylacetamide, DME=1,2-dimethoxyethane, DMF=N,N-dimethylformamide, DMSO=dimethylsulfoxide, EDCI=1-(3-dimethylaminopropyl)-3-ethylcarbodiimide hydrochloride, ESI=electrospray ionisation, EtOAc=ethyl acetate, EtOH=ethanol, Et$_2$O=diethyl ether, h=hour(s), HATU=O-(7-Azabenzotriazol-1-yl)-N,N,N',N'-tetramethyluronium hexafluorophosphate, HCl=hydrochloric acid, H$_2$O=water, HOBt=1-hydroxy-1,2,3-benzotriazole, HPLC=high-performance liquid chromatography, K$_2$CO$_3$=potassium carbonate, KF=potassium fluoride, KHCO$_3$=potassium bicarbonate, LiHMDS=lithium bis(trimethylsilyl)amide, LiOH=lithium hydroxide, MeOH=methanol, MgSO$_4$=magnesium sulfate, min.=minute(s), MPLC=medium pressure liquid chromatography, MS=mass spectrum, Mukaiyama reagent=2-chloro- or 2-bromo-1-methylpyridinium iodide, Na$_2$SO$_4$=sodium sulfate, NaClO$_2$=sodium chlorite; NaCN=sodium cyanide, NaH=sodium hydride, NaHCO$_3$=sodium bicarbonate, NaH$_2$PO$_4$=sodium dihydrogen phosphate, NaOEt=sodium ethoxide, NaOH=sodium hydroxide, NaOMe=sodium methoxide, NEt$_3$=triethylamine, NH$_4$Cl=ammonium chloride, NH$_4$OAc=ammonium acetate, Pd(Ph$_3$P)$_4$=tetrakis(triphenylphosphine)palladium(0), RT=room temperature, TBAF=tetrabutylammonium fluoride, TBTU=O-benzotriazol-1-yl-N,N,N',N'-tetramethyluronium tetrafluoroborate, THF=tetrahydrofuran, TBME=tert-butyl methyl ether, TFA=trifluoroacetic acid, TLC=thin layer chromatography.

Compounds of the general formula IA, wherein $R^4$ is H, $R^7$ is alkyl or cycloalkyl, A is $CR^9R^{10}$, E is $CR^{12}R^{13}$ and n is zero, IB, wherein $R^4$ is alkyl, $R^7$ is alkyl or cycloalkyl, A is $CR^9R^{10}$, E is $CR^{12}R^{13}$ and n is zero, IC, wherein $R^4$ and $R^7$ are H, A is $CR^9R^{10}$, E is $CR^{12}R^{13}$ and n is zero and ID, wherein $R^4$ is alkyl, $R^7$ is H, A is $CR^9R^{10}$, E is $CR^{12}R^{13}$ and n is zero can be prepared for example as outlined in Scheme 1.

Acylation of 2-aminothiophenes II (either commercially available or prepared according to literature procedures or as described in Schemes 4-6) with dicarboxylic acid mono esters 1, either commercially available or prepared according to literature procedures, furnishes compounds IA and IB, respectively (step a). Amide couplings of this type are widely described in the literature and can be accomplished by the usage of coupling reagents such as, e.g., CDI, DCC, HATU, HOBT, TBTU or Mukaiyama reagent in a suitable solvent, e.g., DMF, DMA, CH$_2$Cl$_2$ or dioxane, optionally in the presence of a base (e.g., NEt$_3$, DIPEA (Huenig's base) or DMAP). Alternatively, the carboxylic acids 1 can be converted into their acid chlorides by treatment with, e.g. thionyl chloride, neat or optionally in a solvent such as CH$_2$Cl$_2$. Reaction of the acid chloride with 2-aminothiophenes II in an appropriate solvent such as CH$_2$Cl$_2$ or DMF and a base, e.g. NEt$_3$, Huenig's base, pyridine, DMAP or lithium bis(trimethylsilyl)amide at temperatures ranging from 0° C. to the reflux temperature of the solvent or solvent mixture yields compounds IA and IB, respectively (step a).

Compounds IB can alternatively be prepared through alkylation of compounds IA with compounds of the type $R^4X$, in which X is a suitable leaving group such as chlorine, bromine, iodine, —OSO$_2$alkyl (e.g. mesylate (methanesulfonate), —OSO$_2$fluoroalkyl (e.g. triflate (trifluoromethanesulfonate) or —OSO$_2$aryl (e.g. tosylate (p-toluenesulfonate)) using a suitable base in an appropriate solvent (e.g. sodium hydride in DMF) at temperatures between 0° C. and the boiling temperature of the solvent (step b).

Acylation of 2-aminothiophenes II with carboxylic acid anhydrides 2 (either commercially available or accessible by methods known in the art) in appropriate solvents (e.g. Et$_2$O, THF, dioxane, DMF or CH$_3$CN) furnishes compounds IC and ID. The reaction can be carried out in the presence of a suitable base such as NEt$_3$, Huenig's base, DMAP, DBU or lithium bis(trimethylsilyl)amide (step c).

Compounds IC may be also prepared from compounds IA (step d) for those cases, in which the substituent $R^7$ in compounds of formula IA is a cleavable alkyl group. Cleavage of the ester functionality in IA under basic (e.g. methyl or ethyl esters with lithium or sodium hydroxide in polar solvents such as methanol, H$_2$O or THF or mixtures of said solvents) or under acidic conditions (e.g. a tert-butyl ester using concentrated hydrochloric acid in tetrahydrofuran or formic acid in an appropriate solvent such as alcohols like isopropanol) furnishes compounds IC (step d). Further esters include, but are not limited to, e.g. allyl or benzyl esters that can be cleaved by methods known to those skilled in the art.

Compounds IB can also be prepared from compounds ID through alkylation of ID with compounds $R^7X$ in which X is a suitable leaving group such as chlorine, bromine, iodine, —$OSO_2$alkyl (e.g. mesylate (methanesulfonate), —$OSO_2$fluoroalkyl (e.g. triflate (trifluoromethanesulfonate) or —$OSO_2$aryl (e.g. tosylate (p-toluenesulfonate)) using a suitable base in an appropriate solvent (e.g. sodium hydride in DMF) at temperatures between 0° C. and the boiling temperature of the solvent (step e).

Compounds IC may also be prepared from intermediates 3 by cleavage of the imide applying procedures described in literature (e.g. L. Aurelio et al., *J. Med. Chem.* 2010, 53(18), 6550-6559), for example by using a suitable base and solvent such as NaOH in THF or $H_2O$ and EtOH (step g).

Compounds ID may be also prepared from compounds IB for those cases, in which the substituent $R^7$ in compounds of formula IB is a cleavable alkyl group, using the methods described before (step h).

Intermediates 3 in turn can be obtained by acylation of 2-aminothiophenes II in which $R^4$ is hydrogen through acylation with carboxylic acid anhydrides 2 under the conditions described above (step f).

An alternative synthesis of compounds IA-ID is shown in Scheme 2. Persons skilled in the art will acknowledge that the transformations are only applicable for those compounds that carry groups and substituents, in particular ester functionalities substituted with $R^7$, that are stable and not reactive under the applied reaction conditions.

Gewald reaction using α-cyanoesters 4 in which $R^a$ is a cleavable group such as, e.g. a methyl, ethyl or tert-butyl group, aldehydes ($R^1$ or $R^2$=H) or ketones 5 and elemental sulfur in the presence of a base such as morpholine in a suitable solvent like EtOH furnishes thiophene intermediates 6 (step a).

Protection of the amine functionality with a suitable protective group such as an acetyl group and subsequent cleavage of the ester applying methods known in the art and as described in literature (e.g. Y. Huang et al., *Chem Biol. Drug Des.* 2010, 76, 116-129) gives acid intermediates 7 (steps b, c).

Intermediates 7 can be decarboxylated according to literature procedures (e.g. K. Gewald et al., *Z. Chem.* 1967, 7(5), 186-187; H. Luetjens et al., *J. Med. Chem.* 2003, 46(10), 1870-1877; S. Takada, *J. Med. Chem.* 1988, 31(9), 1738-1745; WO2005/044008), for example using copper and quinoline at elevated temperatures to give intermediates 8 (step d).

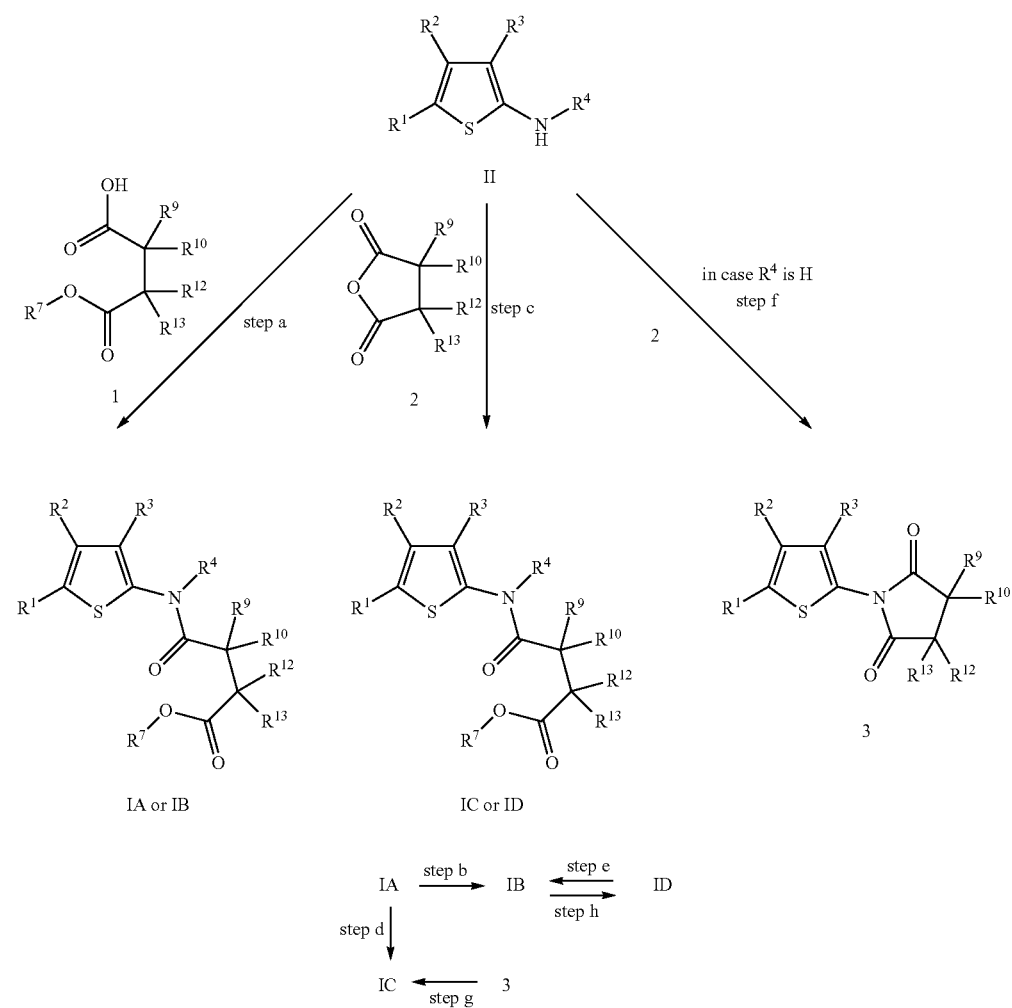

Scheme 1

Removal of the protective group in 8 applying methods known to those skilled in the art and as described in literature yields 2-aminothiophenes 9 (step e).

Acylation of intermediates 9 using the conditions outlined under Scheme 1, with dicarboxylic acid mono esters 1, either commercially available or prepared according to literature procedures, gives intermediates 10 (step f).

Iodination of intermediates 10 using literature procedures (e.g. WO2005/044008) for example using iodine in THF or iodine monochloride in acetic acid yields intermediates 11 (step g).

Cross-coupling reactions of 11 with, e.g. organoboron, -tin or -zinc reagents $R^3M$ furnishes compounds IA (step h). Reactions of this type are widely described in literature (e.g. N. Miyaura (ed.), "Cross-coupling reactions: A practical guide", Curr. Topics Chem. 219). For example, reaction of 11 with (substituted) aryl- or heteroaryl-boronic acids $R^3$—B(OH)$_2$ or boronic esters $R^3$—B(OR')$_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1$^{st}$ Ed., 2005, John Wiley & Sons, New York) using a suitable catalyst (e.g. dichloro[1,1-bis(diphenylphosphino)-ferrocene]palladium(II) CH$_2$Cl$_2$ adduct, tetrakis(triphenylphosphine)palladium(0) or palladium (II) acetate with triphenylphosphine) in an appropriate solvent (e.g. dioxane, DME, H$_2$O, toluene, DMF or mixtures thereof) and a suitable base (e.g. Na$_2$CO$_3$, NaHCO$_3$, KF, potassium carbonate or NEt$_3$) at temperatures between room temperature and the boiling point of the solvent or solvent mixture yields compounds IA (step h). Suzuki reactions of this type are broadly described in literature (e.g. A. Suzuki, N. Miyaura, Chem. Rev. 1979, 95, 2457-2483; A. Suzuki, J. Organomet. Chem. 1999, 576, 147-168; V. Polshettiwar et al., Chem. Sus. Chem. 2010, 3, 502-522) and are well known to those skilled in the art. Alternatively, aryl- or heteroaryl-trifluoroborates $R^3BF_3K$ can be used in the cross-coupling reaction applying a palladium catalyst such as tetrakis-(triphenylphosphine)palladium(0), palladium(II) acetate or dichloro[1,1'-bis(diphenyl-phosphino)ferrocene]palladium(II) CH$_2$Cl$_2$ adduct in the presence of a suitable base such as cesium carbonate or potassium phosphate in solvents such as toluene, THF, dioxane, H$_2$O or mixtures thereof, at temperatures between room temperature and the boiling point of the solvent or solvent mixture.

Compounds IA can be also synthesized by reacting 11 with (substituted) aryl- or heteroaryl tin reagents $R^3$—SnR$_3$ (R=e.g. Me or n-Bu; either commercially available or prepared according to literature procedures) in the presence of a suitable catalyst (e.g. tetrakis(triphenylphosphine)-palladium(0), benzylbis(triphenyl-phosphine)palladium(II) chloride, bis(triphenylphosphine)-palladium(II) dichloride or dichloro[1,1'-bis(diphenylphosphino)ferrocene]palladium (II) CH$_2$Cl$_2$ adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. J. K. Stille, Angew. Chem. Int. Ed. Engl. 1986, 25, 508-524) and well known to those skilled in the art (step h).

Alternatively, compounds IA can be synthesized from reaction of 11 with (substituted) aryl- or heteroaryl zinc halides $R^3$—ZnX (X=Cl, Br or I) (either commercially available or synthesized by methods described in literature) using a nickel (e.g. tetrakis(triphenylphosphine)nickel(0)) or palladium catalyst (e.g. tetrakis(triphenyl-phosphine)palladium (0)) in an appropriate solvent such as THF or DMA in a temperature range between room temperature and boiling point of the solvent. Negishi couplings of this type are broadly described in literature (e.g. "Name Reactions for Homologations—Part I: Negishi cross-coupling reaction", Li, J. J., Corey, E. J., Eds.; Wiley & Sons, Hoboken, N.J., 2009, 70-99; G. Organ, Eur. J. Org. Chem. 2010, 4343-4354) and well known to those skilled in the art (step h).

Compounds IA may then be further converted into compounds IB-ID as described under Scheme 1 (steps i, j, k).

Compounds IB may be also prepared by cross-coupling reactions of intermediates 12 with organoboron, -tin or -zinc reagents $R^3M$ using the coupling conditions described above (step m).

Intermediates 12 are available for example through alkylation of intermediates 11 with an alkylating agent $R^4$—X in which X signifies a suitable leaving group such as chlorine, bromine, iodine, —OSO$_2$alkyl (e.g. mesylate (methanesulfonate), —OSO$_2$fluoroalkyl (e.g. triflate (trifluoromethanesulfonate) or —OSO$_2$aryl (e.g. tosylate (p-toluenesulfonate)) using a suitable base, e.g. sodium hydride in an appropriate solvent such as THF or DMF (step l).

Scheme 2

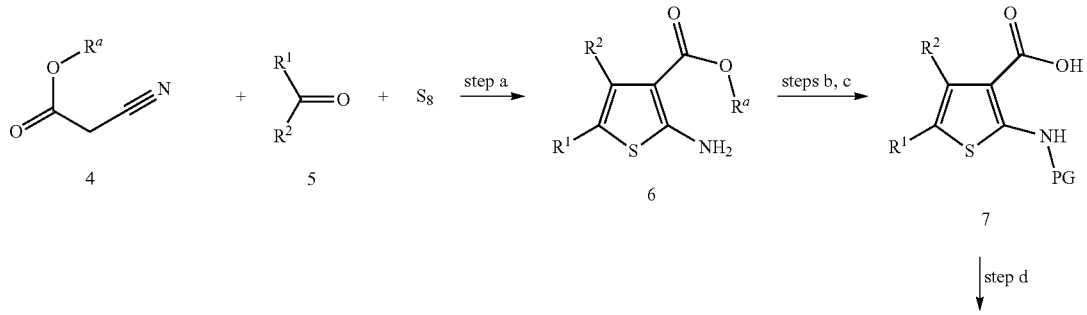

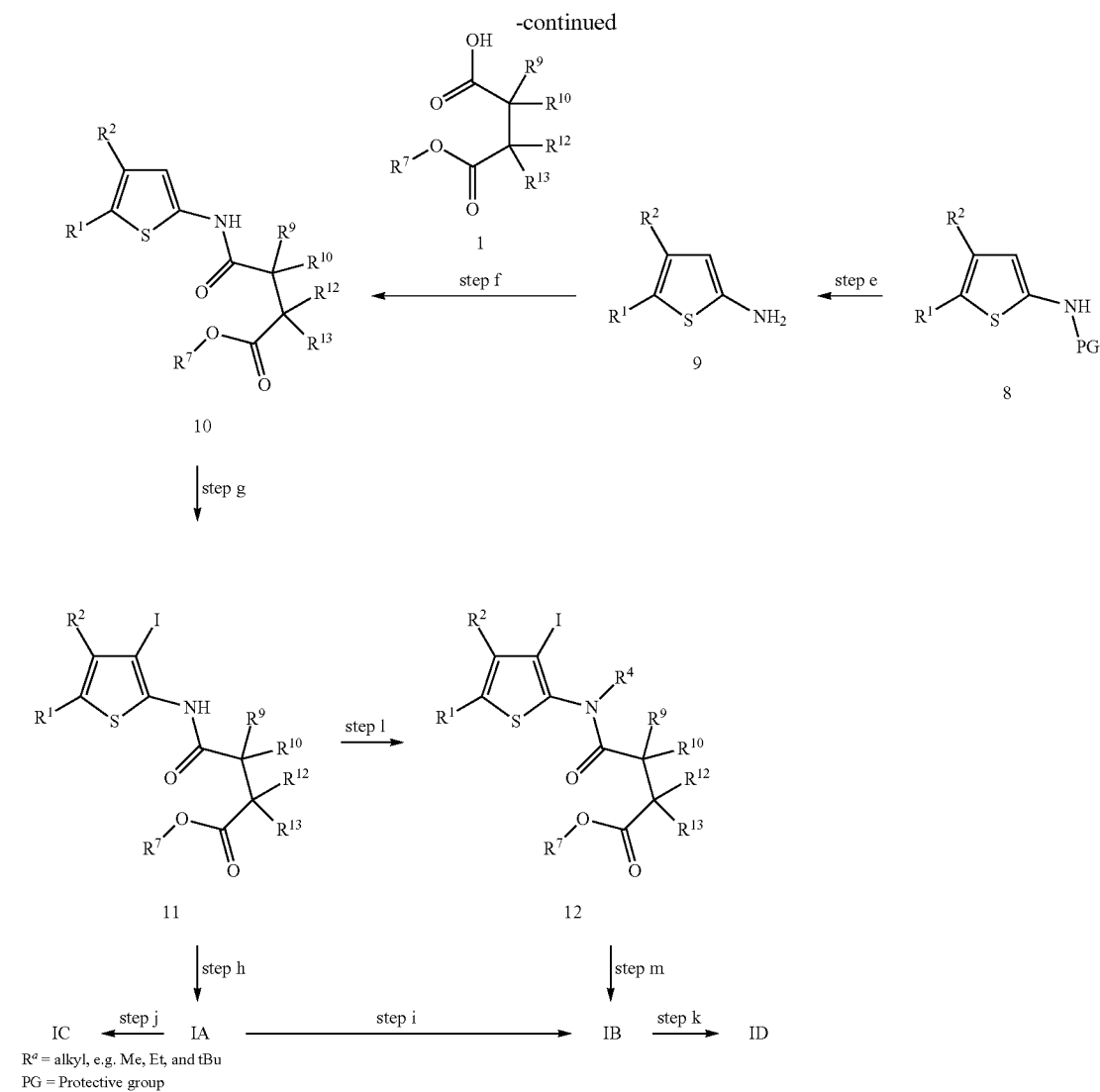

An alternative synthesis of compounds IC from intermediates 9 is shown in Scheme 3.

Acylation of 2-aminothiophene intermediates 9, prepared as described under Scheme 2, with carboxylic acid anhydrides 2 (either commercially available or accessible by methods described in references or by methods known in the art) in appropriate solvents (e.g. Et$_2$O, THF, dioxane, DMF or CH$_3$CN) furnishes intermediates 13. The reaction can be carried out in the presence of a suitable base such as NEt$_3$, Huenig's base, DMAP, DBU or lithium bis(trimethylsilyl) amide (step a).

Iodination of intermediates 13 according to literature procedures (e.g. WO2005/044008) for example using iodine in THF or iodine monochloride in acetic acid, yields intermediates 14 (step b).

Cross-coupling reactions of intermediates 14 with organoboron, -tin or -zinc reagents R$^3$M using the coupling conditions described under Scheme 2 gives intermediates 3 (step c) which can be further converted into compounds IC using the reaction conditions described under Scheme 1 (step d).

Scheme 3

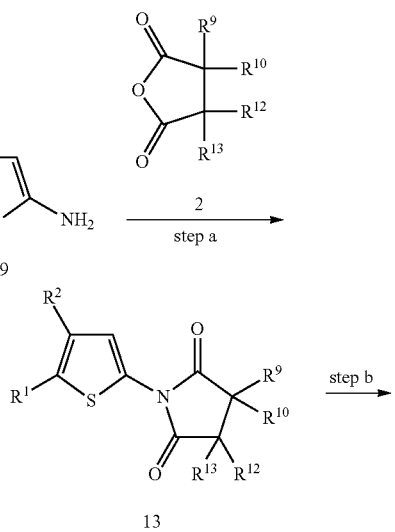

-continued

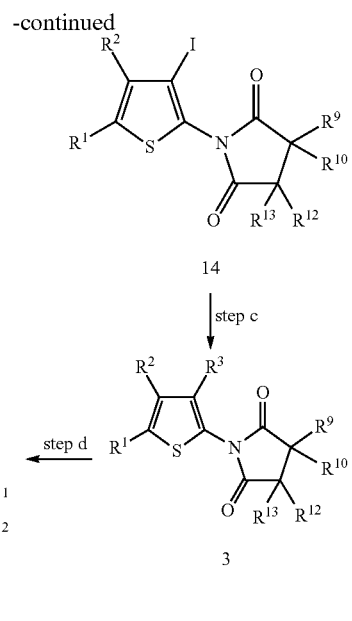

An example for the construction of 2-aminothiophenes IIa, wherein $R^4$ is H, IIb, wherein $R^4$ is methyl and IIc, wherein $R^4$ is alkyl or cycloalkyl, is shown in Scheme 4.

The synthesis of substituted 2-aminothiophenes IIa is broadly described in literature. In particular, the Gewald reaction, a one-pot multi-component condensation between an α-methylene carbonyl compound (cyclic or acyclic ketone or aldehyde), elemental sulfur, a base (e.g. NEt$_3$, morpholine) and an α-activated nitrile (e.g. α-cyanoesters leading to compounds with $R^3$ being an ester group, malonitrile giving compounds in which $R^3$ is cyano, or aryl- or heteroarylacetonitriles leading to compounds with $R^3$ being aryl or heteroaryl) is often applied for the synthesis of poly-substituted 2-aminothiophenes (e.g. K. Gewald et al., *Angew. Chem.* 1961, 73(3), 114-114; K. Gewald et al., *Chem. Ber.* 1965, 98, 3571-3577; K. Gewald et al., *Monatsh. Chem.* 1988, 119, 985-992; R. W. Sabnis et al., *J. Het. Chem.* 1999, 36, 333-345; H. Zhang et al., *Synthesis* 2004, 18, 3055-3059; M. Sridhar et al., *Tetrahedron Lett.*, 2007, 48(18), 3171-3172; Z. Puterová et al., *Arkivoc* 2010(i), 209-246; T. Wang et al., *Synlett* 2010, 1351-1354; DE2627935; WO2005/044008; WO2009/033581).

Gewald reaction as described above using commercially available and appropriately substituted acetonitriles 16, aldehydes ($R^1$ or $R^2$=H) or ketones (in which for the present invention $R^1$ and $R^2$ together do not form a cycle and either $R^1$ or $R^2$ represents an optionally mono-substituted methyl group) 5 and elemental sulfur in the presence of a base such as morpholine yields 2-aminothiophenes IIa (step a).

In cases where the acetonitrile derivatives 16 are commercially not available they may be prepared from compounds 15 in which X is a suitable leaving group such as chlorine, bromine, —OSO$_2$alkyl (e.g. mesylate (methanesulfonate), —OSO$_2$fluoroalkyl (e.g. triflate (trifluoromethanesulfonate) or —OSO$_2$aryl (e.g. tosylate (p-toluenesulfonate) by nucleophilic substitution with sodium or potassium cyanide in an appropriate solvent such as DMSO or DMF at temperatures between 0° C. and the boiling temperature of the solvent (step f). Reactions of this type are known to those skilled in the art and have been described in literature (e.g. M. Katkevics, *Synlett* 2011, 17, 2525-2528; R. Gomez et al., *Bioorg. Med. Chem. Lett.* 2011, 21(24), 7344-7350; F. Fache et al., *Eur. J. Org. Chem.* 2011, 30, 6039-6055; US2012/0015999). In case $R^3$ is an 1,2,4-oxadiazole ring bearing, e.g. an alkyl, cycloalkyl, chloroalkyl or optionally substituted aryl substituent in the 3-position ($R^b$), the acetonitrile derivatives 16 may be prepared from amidoximes 17 (either commercially available or prepared for example by reaction of alkyl, cycloalkyl, chloroalkyl or aryl nitriles with hydroxylamine in analogy to literature procedures, e.g. WO2005/082859; WO2005/076347; WO2008/093960) and commercially available 1-cyanoacetyl-3,5-dimethylpyrazole 18 according to literature procedures (e.g. I. O. Zhuravel et al., *Synthetic Commun.* 2008, 38(21), 3778-3784; A. V. Borisov et al., *J. Comb. Chem.* 2009, 11(6), 1023-1029) (step g).

Alkylation of 2-aminothiophenes IIa with methyliodide or dimethylsulfate using a suitable base and solvent such as potassium carbonate (optionally in the presence of potassium iodide) in CH$_3$CN or CsCO$_3$ in DMF furnishes compounds IIb in which $R^4$ is a methyl group (step b). Microwave irradiation may be applied to accelerate the reaction. Alternatively, compounds IIa can be converted into compounds IIb by reaction of IIa with triethyl orthoformate and subsequent reduction of the resulting ethoxymethylenamino-thiophene intermediate with a suitable reducing agent such as NaBH$_4$ in an appropriate solvent such as EtOH. Reactions of both types are described in literature (e.g. WO2008/154221; WO2011/100838; I. C. Gonzalez et al., *Bioorg. Med. Chem. Lett.* 2004, 14(15), 4037-4043) and are known to those skilled in the art (step b).

2-Aminothiophenes IIb and IIC can be prepared from IIa, for example by first protecting the amine function in IIa with a suitable protective group such as an acetyl or a tert-butoxycarbonyl (Boc) group by methods known in the art and as described in literature to give intermediates 19 (step c).

Alkylation of intermediates 19 with an alkylating agent $R^4$—X in which X signifies a suitable leaving group such as chlorine, bromine, iodine, —OSO$_2$alkyl (e.g. mesylate (methanesulfonate), —OSO$_2$fluoroalkyl (e.g. triflate (trifluoromethanesulfonate) or —OSO$_2$aryl (e.g. tosylate (p-toluenesulfonate)) using a suitable base, e.g. sodium hydride in an appropriate solvent such as THF or DMF furnishes intermediates 20 (step d).

Removal of the protective group in intermediates 20 applying methods known to those skilled in the art and as described in literature gives 2-aminothiophenes IIb and IIc, respectively. Reactions of this type have also been published in literature (e.g. WO2005/044008; P. J. Scammels et al., *Org. Biomol. Chem.* 2011, 9(13), 4886-4902) (step e).

Scheme 4

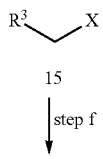

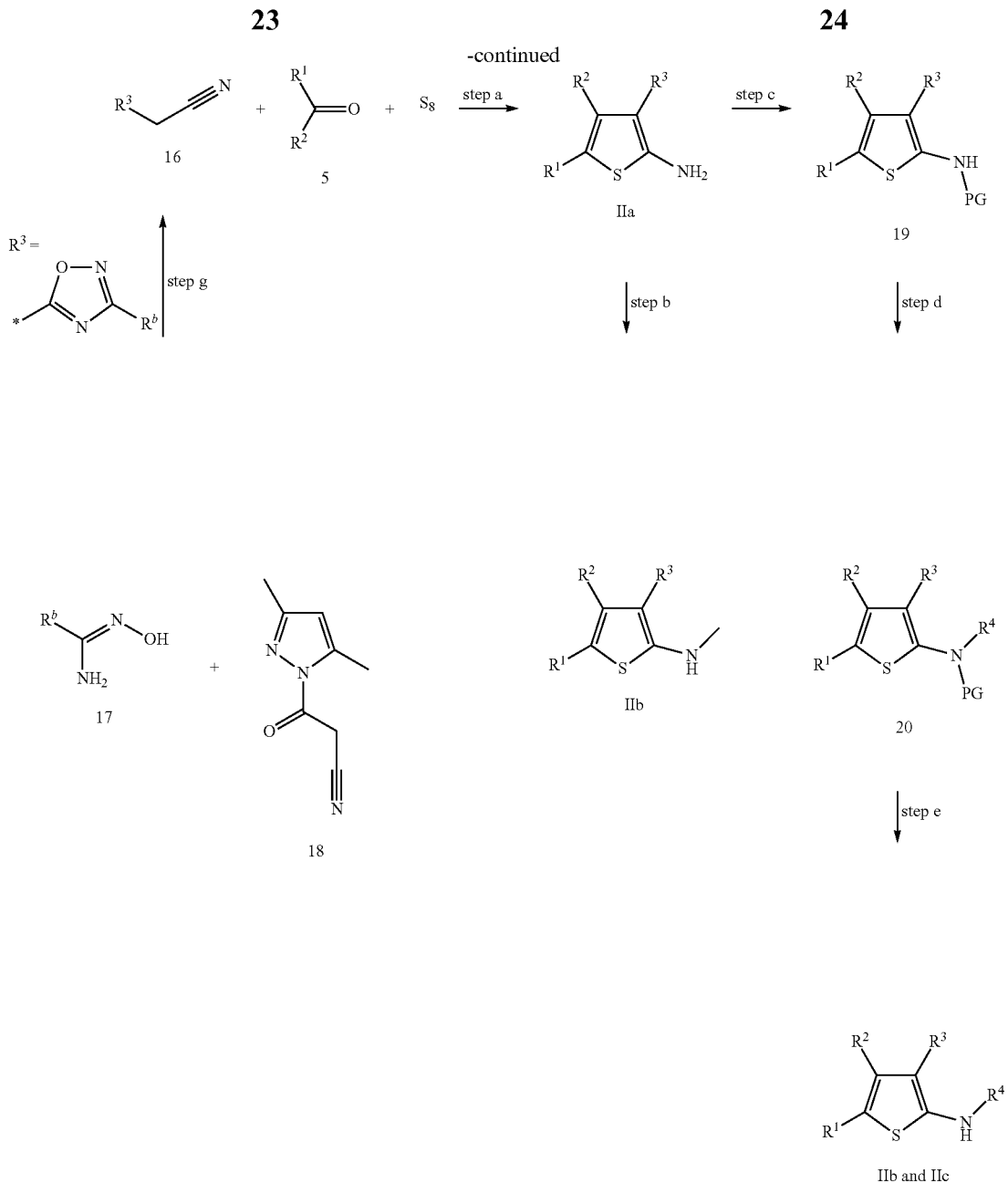

$R^b$ = e.g. alkyl, cycloalkyl, chloroalkyl, (substituted) aryl
PG = Protective group 2-Aminothiophenes IIa-IIc may alternatively also be prepared from intermediates 8 according to Scheme 5.

Iodination of intermediates 8, prepared for example as described under Scheme 2, according to literature procedures (e.g. WO2005/044008), for example using iodine in THF or iodine monochloride in acetic acid, yields intermediates 21 (step a).

Cross-coupling reactions of intermediates 21 with organoboron, -tin or -zinc reagents $R^3M$ using the coupling conditions described under Scheme 2 furnishes intermediates 19 (step b).

Removal of the protective group in 19 applying methods known to those skilled in the art yields 2-aminothiophenes IIa (step c) which can be further converted into compounds IIb according to the procedures described under Scheme 4 (step d).

Intermediates 19 can be transferred into intermediates 20 by reaction with an alkylating agent $R^4$—X in which X signifies a suitable leaving group such as chlorine, bromine, iodine, —OSO$_2$alkyl (e.g. mesylate (methanesulfonate), —OSO$_2$fluoroalkyl (e.g. triflate (trifluoromethanesulfonate) or —OSO$_2$aryl (e.g. tosylate (p-toluenesulfonate)) using a suitable base, e.g. sodium hydride in an appropriate solvent such as THF or DMF (step e).

Removal of the protective group in intermediates 20 applying methods known to those skilled in the art and as described in literature gives 2-aminothiophenes IIb and IIc, respectively.

Scheme 5

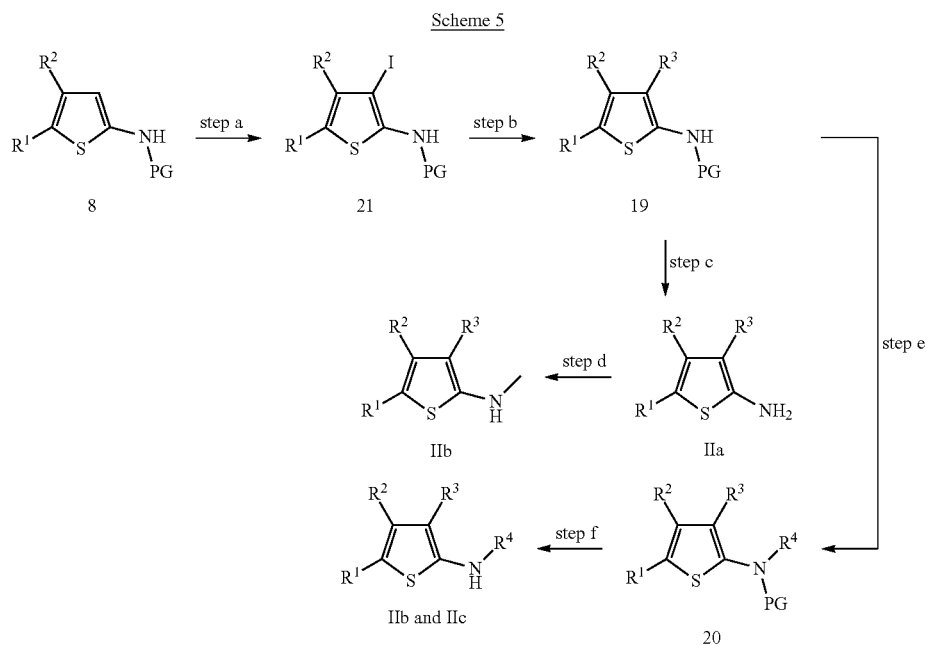

2-Aminothiophenes wherein $R^3$ is heterocycloalkyl or heteroaryl which can be built up from aryl carboxylic acid precursors can also be prepared from thiophene carboxylic acid intermediates such as 7 which in turn can be synthesized for example by the methods described under Scheme 2. The synthesis of heterocyclic ring systems from carboxylic acids is widely described in the literature and well known by those skilled in the art. One example in which $R^3$ is a 3-substituted 1,2,4-oxadiazole ring is shown in Scheme 6.

Reaction of 7 with substituted N'-hydroxycarboximidamides 22 (either commercially available or prepared for example by reaction of nitriles of the type $R^{23}CN$ with hydroxylamine in analogy to literature procedures, e.g. WO2005/082859; WO2005/0076347; WO2008/093960) applying standard coupling conditions using for example EDCI together with HOBT or HATU in a suitable solvent such as DMF (step a) and cyclization of the resulting intermediates 23 using for example TBAF in THF yields intermediates 24 (step b).

Cleavage of the protective group in intermediates 24 using literature methods known by those skilled in the art yields intermediates 25 (step c).

Alkylation of the intermediates 24 by reaction with an alkylating agent $R^4$—X in which X signifies a suitable leaving group such as chlorine, bromine, iodine, —$OSO_2$alkyl (e.g. mesylate (methanesulfonate), —$OSO_2$fluoroalkyl (e.g. triflate (trifluoromethanesulfonate) or —$OSO_2$aryl (e.g. tosylate (p-toluenesulfonate)) using a suitable base, e.g. sodium hydride in an appropriate solvent such as THF or DMF yields intermediates 26 (step d).

Intermediates 27 may be prepared from intermediates 26 through removal of the protective group using literature procedures (step f). Alternatively, alkylation of intermediates 25 using the methods for example described under Scheme 4 gives intermediates 27 (step e).

Scheme 6

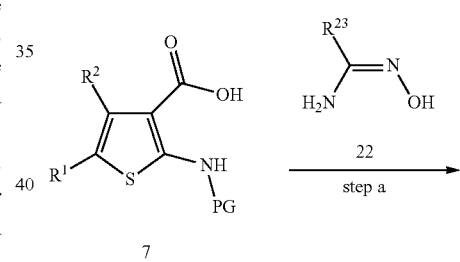

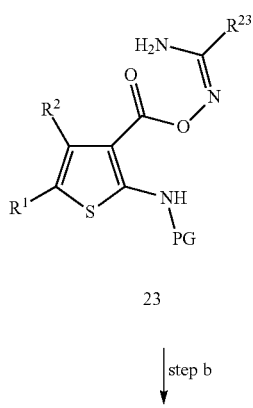

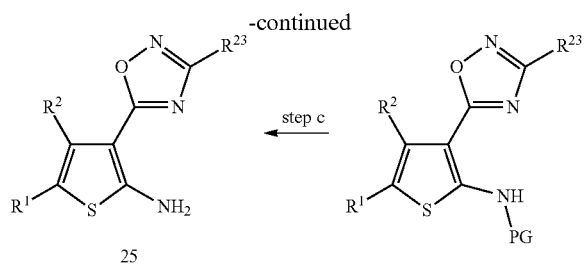

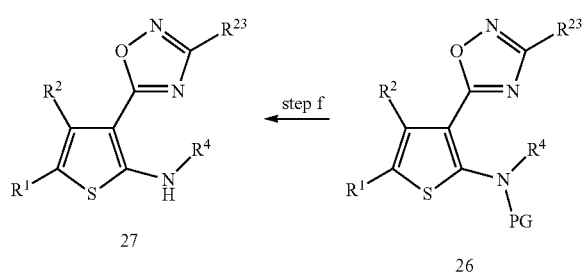

PG = Protective group

Compounds of the general formula I, wherein A is NR$^8$, E is CR$^{12}$R$^{13}$ and n is zero or 1 can be prepared for example according to Scheme 7. Particularly, compounds of formula IE, wherein R$^4$ is H and R$^7$ is alkyl or cycloalkyl, IF, wherein R$^4$ and R$^7$ are H, IG, wherein R$^4$ is H, R$^7$ is alkyl or cycloalkyl and R$^8$ is H, IH, wherein R$^4$ is alkyl, R$^7$ is alkyl or cycloalkyl and R$^8$ is H, IJ, wherein R$^4$, R$^7$ and R$^8$ are H, IK, wherein R$^4$ is alkyl and R$^7$ and R$^8$ are H, IL, wherein R$^4$ is H or alkyl, R$^7$ is alkyl or cycloalkyl and R$^8$ is alkyl, and IM, wherein R$^4$ and R$^7$ are H and R$^8$ is alkyl.

The amino group in 2-aminothiophenes IIa, wherein R$^4$ is H, can be converted into an isocyanate functionality for example by reacting IIa with phosgene or a substitute thereof (e.g. trichloromethyl chloroformate ("diphosgene") or bis (trichloromethyl) carbonate ("triphosgene")) in an appropriate solvent such as THF or CH$_2$Cl$_2$, optionally in the presence of a base such as pyridine or NEt$_3$ to yield intermediates 28 (step a). Transformations of this type are well known in the art and broadly described in literature (e.g. G. N. Anilkumar et al., *Bioorg. Med. Chem. Lett.* 2011, 21(18), 5336-5341; DE3529247; WO2011/140527; WO2011/123937).

Reaction of the isocyanates 28 with appropriately substituted α- or β-amino acids (R$^7$ is H) or esters (R$^7$ is alkyl or cycloalkyl) 29 (n is zero and 1, commercially available or synthesized by methods known in the art) in an appropriate solvent such as toluene, DMF or CH$_2$Cl$_2$ optionally in the presence of a suitable base such as NEt$_3$ or Huenig's base gives compounds IE and IF, respectively (step b). Additions of primary or secondary amines to isocyanates are described in literature (e.g. W. J. McClellan et al., *Bioorg. Med. Chem. Lett.* 2011, 21(18), 5620-5624; J. Regan et al., *J. Med. Chem.* 2002, 45(14), 2994-3008; U.S. Pat. No. 4,314,842; WO2006/067385) and are well known to those skilled in the art.

Compounds IF can alternatively be synthesized from compounds IE for those cases, in which the substituent R$^7$ in compounds of formula IE is a cleavable alkyl group, using the methods described under Scheme 1 (step c).

2-Aminothiophenes II can be reacted with isocyanates 30 (either commercially available or synthesized by methods known in the art) in an appropriate solvent such as toluene, DMF or CH$_2$Cl$_2$ optionally in the presence of a suitable base such as NEt$_3$ or Huenig's base to give compounds IG and IH, respectively (step d).

In case R$^7$ in compounds IG and IH is a cleavable ester group, it can be cleaved applying procedures known in the art and as published to yield compounds IJ and IK, respectively (step e).

Compounds IL may be synthesized through alkylation of compounds IH with compounds of the type R$^8$X, in which X is a suitable leaving group such as chlorine, bromine, iodine, —OSO$_2$alkyl (e.g. mesylate (methanesulfonate), —OSO$_2$fluoroalkyl (e.g. triflate (trifluoromethanesulfonate) or —OSO$_2$aryl (e.g. tosylate (p-toluenesulfonate)) using a suitable base in an appropriate solvent (e.g. sodium hydride in DMF) at temperatures between 0° C. and the boiling temperature of the solvent (step f).

In case R$^7$ in compounds IL is a cleavable ester group, it can be cleaved applying procedures known by those skilled in the art and as described in literature to yield compounds IM (step g).

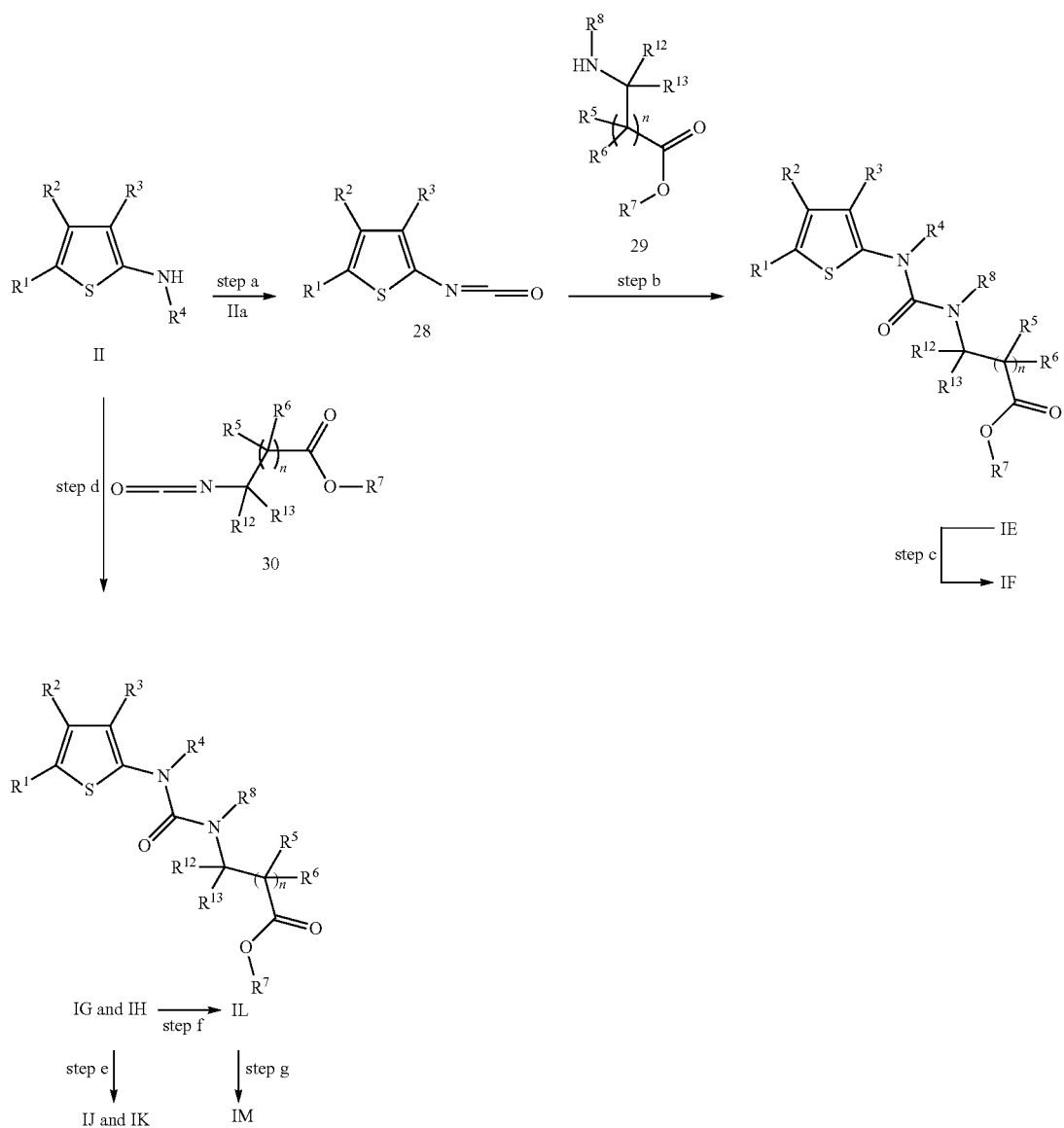

Compounds IN, wherein A is $CR^8R^9$, E is $NR^{11}$, n is 1 and $R^7$ is alkyl or cycloalkyl, and IO, wherein A is $CR^8R^9$, E is $NR^{11}$, n is 1 and $R^7$ is H can be prepared for example as shown in Scheme 8.

Compounds IN can be synthesized for example through acylation of 2-aminothiophenes II with appropriately substituted (alkoxycarbonylmethyl-amino)-acetic acid or (cycloalkoxycarbonylmethyl-amino)-acetic acid derivatives 31 (either commercially available or synthesized by methods known in the art), using literature procedures and the methods described under Scheme 1.

If $R^7$ in compounds IN is a cleavable ester group it can be cleaved applying procedures known by those skilled in the art and as described in literature to yield compounds IO (step b).

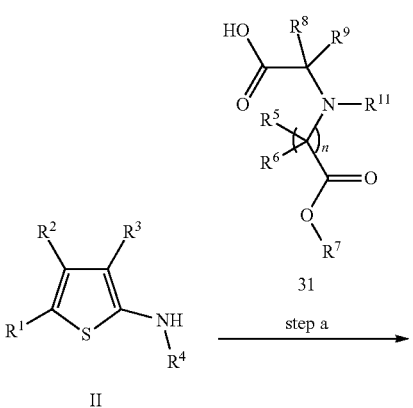

-continued

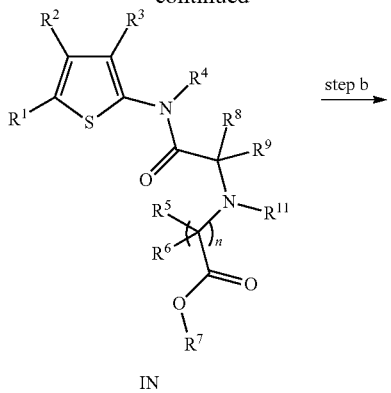

IN step b

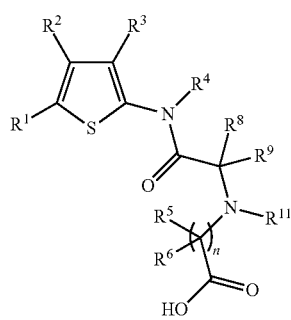

IO

Also an embodiment of the present invention is a process to prepare a compound of formula (I) as defined above comprising the reaction of a) a compound of formula (II) in the presence of a compound of formula (V);

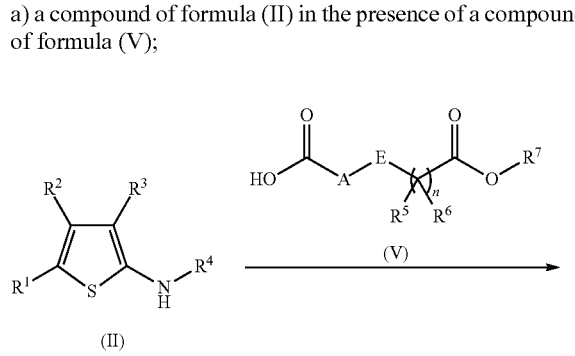

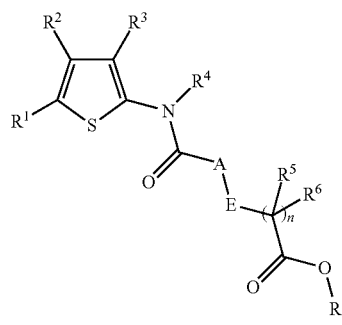

(I)

b) a compound of formula (II) in the presence of a compound of formula (VI);

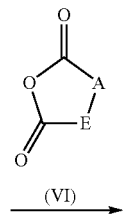

(II)

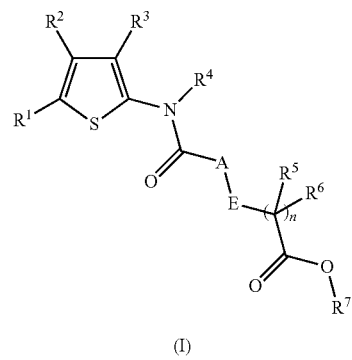

(VI)

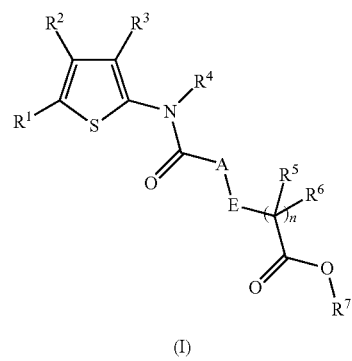

(I)

C) a compound of formula (VII) in the presence of a compound of formula (VIII);

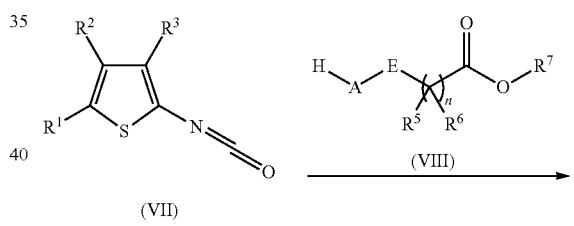

or
d) a compound of formula (II) in the presence of a compound of formula (IX);

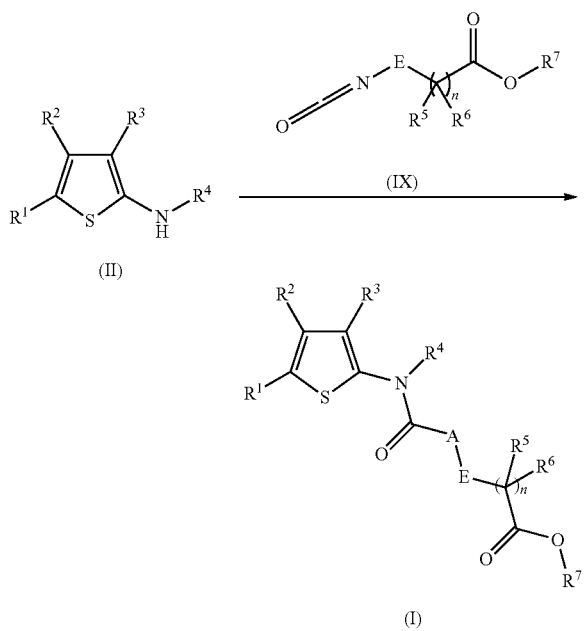

wherein $R^1$, $R^2$, $R^3$, $R^4$, $R^5$, $R^6$ are as defined above and wherein $R^7$ is alkyl or cycloalkyl and A is $CR^9R^{10}$ in step a), A is $CR^9R^{10}$, E is $CR^{12}R^{13}$ and n is zero in step b), $R^4$ is H and A is $NR^8$ in step c) and $R^4$ is H, A is $NR^8$, E is $CR^{12}R^{13}$ and n is 1 in step d).

Also a further preferred embodiment of the present invention is a process to prepare a compound of formula (I) as defined above comprising the reaction of a compound of formula (II) in the presence of a compound of formula (VI).

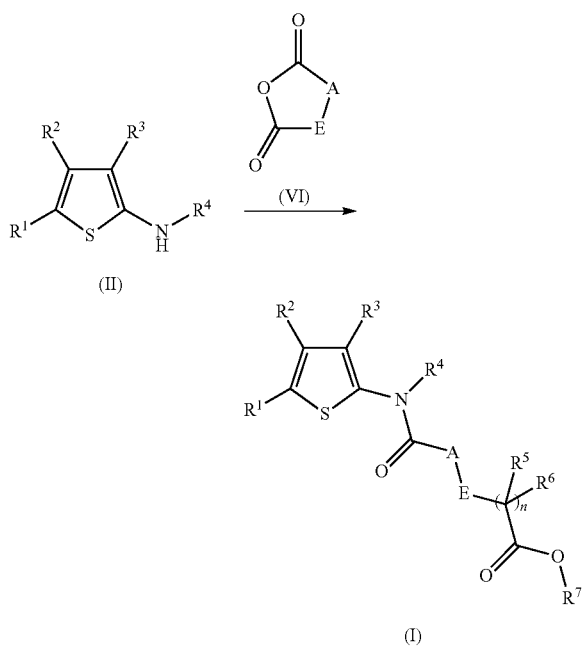

wherein $R^1$, $R^2$, $R^3$, $R^4$, $R^5$, $R^6$, $R^7$ and n are as defined above and wherein A is $CR^9R^{10}$ and E is $CR^{12}R^{13}$. In particular in the presence of a solvent, particularly $CH_3CN$, THF or $Et_2O$, in the presence or not of a base, particularly in the presence of DMAP, DIPEA or DBU, at a temperature comprised between 0° C. and reflux, particularly between RT and reflux.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

In accordance with the invention, the compounds of formula (I) or their pharmaceutically acceptable salts and esters can be used for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

Particular liver diseases are liver diseases involving inflammation, steatosis and/or fibrosis, such non-alcoholic fatty liver disease, more particularly non-alcoholic steatohepatitis.

Particular lipodystrophy is genetic and iatrogenic lipodystrophy.

Particular eye diseases are eye diseases supported by endothelial proliferation and angiogenesis, particularly macular degeneration and retinopathy.

Particular lung diseases are asthma, bronchopulmonary dysplasia and chronic obstructive pulmonary disease.

Particular chronic renal diseases are vasculitis, focal segmental glomerulosclerosis, diabetic nephropathy, lupus nephritis, polycystic kidney disease and drug or toxin-induced chronic tubulointerstitial nephritis.

The present invention also relates to the use of a compound according to formula (I) as described herein for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

The present invention particularly relates to the use of a compound according to formula (I) as described herein for the treatment or prophylaxis of type 2 diabetes, atherosclerosis, cancer, chronic renal disease and non-alcoholic steatohepatitis.

The present invention also relates to the use of a compound according to formula (I) as described herein for the treatment or prophylaxis of non-alcoholic steatohepatitis.

A particular embodiment of the present invention is a compound according to formula (I) as described herein for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

Another particular embodiment of the present invention is a compound according to formula (I) as described herein for the treatment or prophylaxis of type 2 diabetes, atherosclerosis, cancer, chronic renal disease and non-alcoholic steatohepatitis.

Also a particular embodiment of the present invention is a compound according to formula (I) as described herein for the treatment or prophylaxis of non-alcoholic steatohepatitis.

The present invention also relates to the use of a compound according to formula (I) as described herein for the preparation of a medicament for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

The present invention particularly relates to the use of a compound according to formula (I) as described herein for the preparation of a medicament for the treatment or prophylaxis of type 2 diabetes, atherosclerosis, cancer, chronic renal disease and non-alcoholic steatohepatitis.

Also an embodiment of the present invention is the use of a compound according to formula (I) as described herein for the preparation of a medicament for the treatment or prophylaxis of non-alcoholic steatohepatitis.

Also an object of the invention is a method for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome, which method comprises administering an effective amount of a compound according to formula (I) as described herein.

Another object of the invention is a method for the treatment or prophylaxis of type 2 diabetes, atherosclerosis, cancer, chronic renal disease and non-alcoholic steatohepatitis, which method comprises administering an effective amount of a compound according to formula (I) as described herein.

Also an embodiment of the present invention is a method for the treatment or prophylaxis of non-alcoholic steatohepatitis, which method comprises administering an effective amount of a compound according to formula (I) as described herein.

Also an embodiment of the present invention is a method for the treatment or prophylaxis of lipodystrophy, which method comprises administering an effective amount of a compound according to formula (I) as described herein.

Also a particular embodiment of the present invention is a compound according to formula (I) as described herein, when manufactured according to any one of the described processes.

Assay Procedures

Compounds were profiled for activity against human FABP4 (huFABP4) and/or human FABP5 (huFABP5) in Terbium (Tb) time resolved-fluorescence energy transfer (TR-FRET) assays monitoring the direct binding of Bodipy labeled fatty acid to His6 tagged FABP proteins (huFABP4 was expressed in house in *E. coli* and purified, huFABP5 was purchased from Cayman Chemical Co., cat. no. 10010364), bound to Terbium labeled anti His6 tag antibody. Assay readouts reflected energy transfer, upon binding of the ligand to the FABP protein, from the Terbium donor molecule to the acceptor Bodipy moiety. Final ligand concentration (125 nM) approximated the Kd for each protein.

Stock DMSO solutions (1.8 mM) of compounds were serially diluted 3-fold for ten concentrations with 100% DMSO (50 μM to 0.003 μM final compound concentration). 1 μl of these compound dilutions and 1 μl of Bodipy labeled fatty acid 4.5 μM in 100% DMSO (Bodipy FL C11, cat. no. D3862, Invitrogen) were sequentially pipetted in wells of 384-well black polypropylene plates (Thermo Matrix cat. no. 4344). FABP4 or FABP5 protein was then added (28 μl of 64 nM protein in 25 mM Tris pH 7.5, 0.4 mg/ml α-globulin, 1 mM DTT, 0.012% NP40, final protein concentration: 50 nM). Assay blanks contained ligand, but no protein. Neutral controls contained ligand, but no compound. After adding the detection reagent (Tb antiHis6 antibody, Columbia Biosciences, TB-110, 6 μl of a 24 nM Ab solution in 25 mM Tris pH 7.5, 0.4 mg/ml γ-globulin, final Tb antiHis6 Ab concentration: 4 nM), plates were spun one minute at 1000 rpm. Following an incubation at room temperature with shaking for 30 minutes, plates were read using an Envision reader (Perkin Elmer, Extinction wavelength: 340 nm, Emission: 490 nm and 520 nm, time delay: 100 μs; time window: 200 μs, 50 flashes).

Final assay conditions were: 50 nM FABP protein, 125 nM Bodipy labeled fatty acid, 0.009% (vol/vol) NP40, 5.5% (vol/vol) DMSO in a total final assay volume of 36 μl. The assay was performed in triplicate.

The relative fluorescence units (RFU) ratio (520 nm*10000/488 nm) were used to calculate the percent inhibition: 100−(RFU ratio compound−blank)/neutral control−blank)*100. These percent inhibition values were then fit to dose response curves using a 4 parameter logistic model (Hill sigmoidal dose-response model). $IC_{50}$s reflected compound concentrations associated with 50% inhibition of protein activity compared to that of neutral controls.

| Example | IC50 h-fabp4-ecoli-r μM | IC50 h-fabp5-ecoli-r μM | Example | IC50 h-fabp4-ecoli-r μM | IC50 h-fabp5-ecoli-r μM |
|---|---|---|---|---|---|
| 1 | 0.2 | 14.8 | 6.2 | 0.09 | 0.06 |
| 2 | 6.16 | 2.46 | 6.3 | 0.105 | 0.227 |
| 3 | 0.07 | 0.12 | 6.4 | 0.02 | 0.06 |
| 3.1 | 0.03 | 0.06 | 6.5 | 0.25 | 0.13 |
| 3.2 | 0.02 | 0.09 | 6.6 | 3.3259 | 2.7097 |
| 3.3 | 0.01 | 0.03 | 6.7 | 0.0408 | 0.1258 |
| 3.4 | 0.21 | 0.05 | 6.8 | 0.0192 | 0.0388 |
| 4 | 0.31 | 0.3 | 6.9 | 0.015 | 0.0986 |
| 4.1 | 0.14 | 0.32 | 6.10 | 0.2476 | 0.189 |
| 4.2 | 0.02 | 0.03 | 6.11 | 0.0205 | 0.0409 |
| 4.3 | 0.02 | 0.04 | 6.12 | 0.0581 | 0.33 |
| 4.4 | 0.04 | 0.05 | 4.6 | 0.044 | 0.066 |
| 4.5 | 0.01 | 0.03 | 4.7 | 0.011 | 0.038 |
| 5 | 0.01 | 0.03 | 4.8 | 0.085 | 0.061 |
| 6 | 0.02 | 0.38 | 4.9 | 0.027 | 0.022 |
| 6.1 | 0.01 | 0.89 | 4.10 | 0.022 | 0.030 |
| 4.11 | 0.031 | 0.039 | 4.16 | 0.023 | 0.031 |
| 4.12 | 0.029 | 0.031 | 4.17 | 0.019 | 0.040 |
| 4.13 | 0.013 | 0.022 | 8 | 0.107 | 0.76 |
| 4.14 | 0.025 | 0.041 | 9 | 0.021 | 0.143 |
| 4.15 | 0.013 | 0.016 | 10 | 0.217 | 6.963 |
| 7 | 0.345 | 0.822 | | | |
| 7.1 | 0.244 | 0.453 | | | |

Compounds of formula (I) and their pharmaceutically acceptable salts or esters thereof as described herein have $IC_{50}$ (FABP4 inhibition) values between 0.000001 μM and 1000 μM, particular compounds have $IC_{50}$ values between 0.000005 μM and 500 μM, further particular compounds have $IC_{50}$ values between 0.00005 μM and 5 μM.

Compounds of formula (I) and their pharmaceutically acceptable salts or esters thereof as described herein have $IC_{50}$ (FABP5 inhibition) values between 0.000001 μM and 1000 μM, particular compounds have $IC_{50}$ values between 0.000005 μM and 500 μM, further particular compounds have $IC_{50}$ values between 0.00005 μM and 50 μM.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of type 2 diabetes related microvascular complications (such as, but not limited to diabetic retinopathy, diabetic neuropathy and diabetic nephropathy), coronary artery disease, obesity and underlying inflammatory diseases, chronic inflammatory and autoimmune/inflammatory diseases.

The invention is illustrated hereinafter by Examples, which have no limiting character.

In case the preparative examples are obtained as a mixture of enantiomers, the pure enantiomers can be separated by methods described herein or by methods known to the person skilled in the art, such as e.g. chiral chromatography or crystallization.

EXAMPLES

All examples and intermediates were prepared under argon atmosphere if not specified otherwise.

Example 1

2-(3-Phenyl-thiophen-2-ylcarbamoyl)-cyclopent-1-enecarboxylic acid

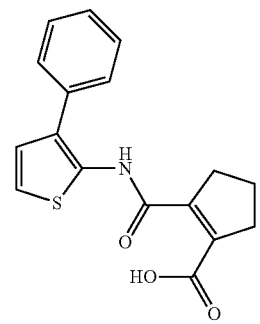 [SMILES: O=C(O)C1=C(C(=O)Nc2sccc2-c2ccccc2)CCC1]

3-Phenyl-thiophen-2-ylamine (73 mg, 417 μmol, Int1.1), NEt$_3$ (84.3 mg, 116 μL, 833 μmol) and 1-cyclopentene-1,2-dicarboxylic anhydride (144 mg, 1.04 mmol) were dissolved in dry THF (3 mL). The green-yellow suspension was stirred at RT over the week-end and filtered. The filtrate was concentrated in vacuo and the residue was purified by preparative HPLC (MeOH/H$_2$O with 0.1% formic acid) to give the title compound as a yellow oil (47 mg, 32%, purity estimated at 90%). MS (ESI): m/z=312.2 [M−H]$^-$.

Example 2

5-[(3-Carboxy-bicyclo[2.2.2]oct-2-ene-2-carbonyl)-amino]-3-methyl-4-(4-methyl-thiazol-2-yl)-thiophene-2-carboxylic acid methyl ester

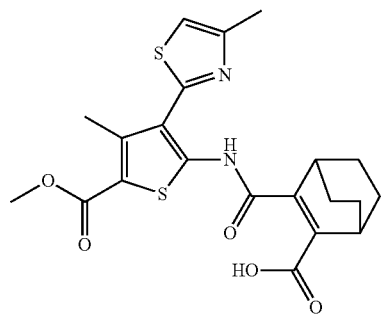 [SMILES: COC(=O)c1sc(NC(=O)C2=C(C(=O)O)C3CCC2CC3)c(-c2nc(C)cs2)c1C]

To the solution of methyl 5-amino-3-methyl-4-(4-methylthiazol-2-yl)thiophene-2-carboxylate (61 mg, 227 μmol, Int1.2) in CH$_3$CN (7 mL) were added DMAP (55.5 mg, 455 μmol) and bicyclo[2.2.2]oct-2-ene-2,3-dicarboxylic anhydride (40.5 mg, 227 μmol, CAS RN 151813-29-5). After stirring at RT for 3 h, the reaction mixture was stirred at 65° C. overnight. The reaction mixture was extracted with EtOAc and 1M aqueous HCl, the organic layer was dried over Na$_2$SO$_4$, filtered and evaporated. The compound was purified by silica gel chromatography using a mixture of CH$_2$Cl$_2$:MeOH (20:1 v/v) as eluant. Brown solid. MS (ESI): m/z=447.1 [M+H]$^+$.

Example 3

2-[4-Cyclopropyl-5-methyl-3-(3-methyl-[1,2,4]oxadiazol-5-yl)-thiophen-2-ylcarbamoyl]-cyclopent-1-enecarboxylic acid

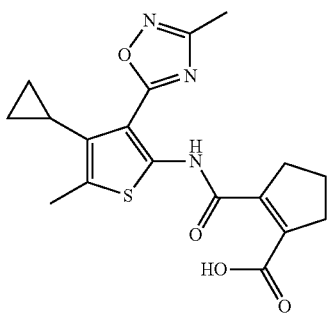 [SMILES: Cc1noc(-c2c(NC(=O)C3=C(C(=O)O)CCC3)sc(C)c2C2CC2)n1]

To a solution of 4-cyclopropyl-5-methyl-3-(3-methyl-[1,2,4]oxadiazol-5-yl)-thiophen-2-ylamine (100 mg, 425 μmol, Int1.3) in CH$_3$CN (8 mL) was added DBU (129 mg, 127 μL, 850 μmol) and 1-cyclopentene-1,2-dicarboxylic anhydride (64.6 mg, 467 μmol, CAS RN 3205-94-5) and the dark solution was stirred at 65° C. for 18 h. The reaction mixture was concentrated under vacuum and the residue was purified by preparative HPLC (Gemini NX column) with a gradient of MeOH:H$_2$O (containing 0.1% formic acid) (80:20 to 98:2). Yellow solid (69 mg, 44%). MS (ESI): m/z=374.117 [M+H]$^+$.

The examples in Table 1 were prepared according to the methods used in example 3, using the 2-aminothiophene and carboxylic acid anhydride reagents as listed in Table 1.

TABLE 1

| No. | Systematic name/ Structure | 2-Aminothiophene | Carboxylic acid anhydride | MS m/z |
|---|---|---|---|---|
| 3.1 | 3-[4-Cyclopropyl-5-methyl-3-(3-trifluoromethyl-[1,2,4]oxadiazol-5-yl)-thiophen-2-ylcarbamoyl]-bicyclo[2.2.2]oct-2-ene-2-carboxylic acid | 4-Cyclopropyl-5-methyl-3-(3-trifluoromethyl-[1,2,4]oxadiazol-5-yl)-thiophen-2-ylamine (Int1.4) | Bicyclo[2.2.2]oct-2-ene-2,3-dicarboxylic anhydride (CAS RN 151813-29-5) | 468.120 [M + H]$^+$ |
| 3.2 | 2-[3-(3-Cyclopropyl-[1,2,4]oxadiazol-5-yl)-4,5-dimethyl-thiophen-2-ylcarbamoyl]-cyclohex-1-enecarboxylic acid | 3-(3-Cyclopropyl-[1,2,4]oxadiazol-5-yl)-4,5-dimethyl-thiophen-2-ylamine (Int1.5) | 1-Cyclohexene-1,2-dicarboxylic anhydride (CAS RN 2426-02-0) | 388.132 [M + H]$^+$ |
| 3.3 | 2-[5-Cyclopropyl-3-(3-cyclopropyl-[1,2,4]oxadiazol-5-yl)-4- | 5-Cyclopropyl-3-(3-cyclopropyl-[1,2,4]oxadiazol- | 1-Cyclopentene-1,2-dicarboxylic anhydride (CAS | 400.133 [M + H]$^+$ |

TABLE 1-continued

| No. | Systematic name/ Structure | 2-Amino-thiophene | Carboxylic acid anhydride | MS m/z |
|---|---|---|---|---|
| | methyl-thiophen-2-ylcarbamoyl]-cyclopent-1-ene carboxylic acid | 5-yl)-4-methyl-thiophen-2-ylamine (Int1.6) | RN 3205-94-5) | |
| 3.4 | 3-[5-Cyclopropyl-3-(3-cyclopropyl-[1,2,4]oxadiazol-5-yl)-4-methyl-thiophen-2-ylcarbamoyl]-bicyclo[2.2.2]oct-2-ene-2-carboxylic acid | 5-Cyclopropyl-3-(3-cyclopropyl-[1,2,4]oxadiazol-5-yl)-4-methyl-thiophen-2-ylamine (Int1.6) | Bicyclo[2.2.2]oct-2-ene-2,3-dicarboxylic anhydride (CAS RN 151813-29-5) | 440.164 [M + H]+ |

Example 4

2-[4-Cyclopropyl-5-methyl-3-(3-methyl-[1,2,4]oxadiazol-5-yl)-thiophen-2-ylcarbamoyl]-cyclohex-1-enecarboxylic acid

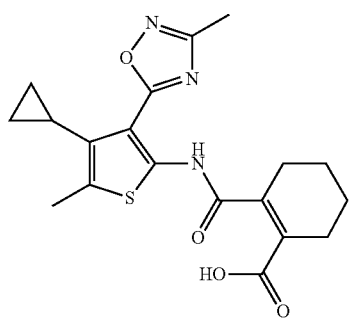 [SMILES: Cc1noc(-c2c(NC(=O)C3=C(C(=O)O)CCCC3)sc(C)c2C2CC2)n1]

To a solution of 4-cyclopropyl-5-methyl-3-(3-methyl-[1,2,4]oxadiazol-5-yl)-thiophen-2-ylamine (85 mg, 361 µmol, Int1.3) in Et$_2$O (3 mL) was added 1-cyclohexene-1,2-dicarboxylic anhydride (55.0 mg, 361 µmol, CAS RN 2426-02-0) and DMAP (2.21 mg, 18.1 µmol). The reaction mixture was stirred at RT for 18 h and then concentrated under vacuum. The residue was purified by preparative HPLC (Gemini NX column) with a gradient of MeOH:H$_2$O (containing 0.1% formic acid) (80:20 to 98:2). Light yellow solid (17 mg, 12.1%). MS (ESI): m/z=388.133 [M+H]+.

The examples in Table 2 were prepared according to the methods used in example 4, using the 2-aminothiophene and carboxylic acid anhydride reagents as listed in Table 2.

TABLE 2

| No. | Systematic name/ Structure | 2-Amino-thiophene | Carboxylic acid anhydride | MS m/z |
|---|---|---|---|---|
| 4.1 | 3-[4-Cyclopropyl-5-methyl-3-(3-methyl-[1,2,4]oxadiazol-5-yl)-thiophen-2-ylcarbamoyl]-bicyclo[2.2.2]oct-2-ene-2-carboxylic acid | 4-Cyclopropyl-5-methyl-3-(3-methyl-[1,2,4]oxadiazol-5-yl)-thiophen-2-ylamine (Int1.3) | Bicyclo[2.2.2]oct-2-ene-2,3-dicarboxylic anhydride (CAS RN 151813-29-5) | 414.148 [M + H]+ |
| 4.2 | 2-[4-Cyclopropyl-3-(3-cyclopropyl-[1,2,4]oxadiazol-5-yl)-5-methyl-thiophen-2-ylcarbamoyl]-cyclopent-1-ene carboxylic acid | 4-Cyclopropyl-5-methyl-3-(3-methyl-[1,2,4]oxadiazol-5-yl)-thiophen-2-ylamine (Int1.7) | 1-Cyclopentene-1,2-dicarboxylic anhydride (CAS RN 3205-94-5) | 400.133 [M + H]+ |
| 4.3 | 3-[4-Cyclopropyl-3-(3-cyclopropyl-[1,2,4]oxadiazol-5-yl)-5-methyl-thiophen-2-ylcarbamoyl]-bicyclo[2.2.2]oct-2-ene-2-carboxylic acid | 4-Cyclopropyl-3-(3-cyclopropyl-[1,2,4]oxadiazol-5-yl)-5-methyl-thiophen-2-ylamine (Int1.7) | Bicyclo[2.2.2]oct-2-ene-2,3-dicarboxylic anhydride (CAS RN 151813-29-5) | 440.163 [M + H]+ |
| 4.4. | 3-[3-(3-Cyclopropyl-[1,2,4]oxadiazol-5-yl)-4,5-dimethyl-thiophen-2-ylcarbamoyl]-bicyclo[2.2.2]oct-2-ene-2-carboxylic acid | 3-(3-Cyclopropyl-[1,2,4]oxadiazol-5-yl)-4,5-dimethyl-thiophen-2-ylamine (Int1.5) | Bicyclo[2.2.2]oct-2-ene-2,3-dicarboxylic anhydride (CAS RN 151813-29-5) | 414.148 [M + H]+ |

TABLE 2-continued

| No. | Systematic name/ Structure | 2-Amino-thiophene | Carboxylic acid anhydride | MS m/z |
|---|---|---|---|---|
| 4.5 | 2-[3-(3-Cyclopropyl-[1,2,4]oxadiazol-5-yl)-4,5-dimethyl-thiophen-2-ylcarbamoyl]-cyclopent-1-enecarboxylic acid | 3-(3-Cyclopropyl-[1,2,4]oxadiazol-5-yl)-4,5-dimethyl-thiophen-2-ylamine (Int1.5) | 1-Cyclopentene-1,2-dicarboxylic anhydride (CAS RN 3205-94-5) | 374.117 [M + H]$^+$ |

Example 5

2-[4-Cyclopropyl-5-methyl-3-(3-trifluoromethyl-[1,2,4]oxadiazol-5-yl)-thiophen-2-ylcarbamoyl]-cyclopent-1-enecarboxylic acid

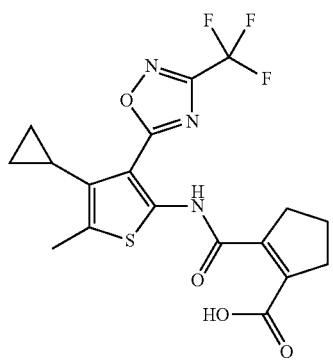 [SMILES: Cc1sc(NC(=O)C2=C(C(=O)O)CCC2)c(-c2nc(C(F)(F)F)no2)c1C1CC1]

To a solution of 2-[4-cyclopropyl-5-methyl-3-(3-trifluoromethyl-[1,2,4]oxadiazol-5-yl)-thiophen-2-ylcarbamoyl]-cyclopent-1-enecarboxylic acid methyl ester (80 mg, 181 μmol, intermediate 7) in dioxane (3 mL) was added H$_2$O (3 mL) and LiOH monohydrate (9.51 mg, 227 μmol) and the resulting clear solution was stirred at RT for 8 h. The reaction mixture was poured on 100 mL 1M aqueous HCl and 100 mL EtOAc and the layers were separated. The aqueous layer was extracted a second time with 100 mL EtOAc. The organic layers were washed with 100 mL brine, dried over MgSO$_4$, filtered and concentrated under vacuum. The compound was purified by silica gel chromatography on a 20 g column using an MPLC (Flashmaster) system eluting with a gradient of CH$_2$Cl$_2$:MeOH (100:0 to 80:20). Yellow solid (57 mg, 74%). MS (ESI): m/z=428.088 [M+H]$^+$.

Example 6

2-[3-(3-Cyclopropyl-[1,2,4]oxadiazol-5-yl)-5-methyl-thiophen-2-ylcarbamoyl]-cyclopent-1-enecarboxylic acid

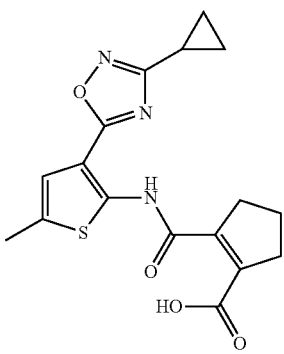 [SMILES: Cc1cc(-c2nc(C3CC3)no2)c(NC(=O)C2=C(C(=O)O)CCC2)s1]

To a solution of 3-(3-cyclopropyl-[1,2,4]oxadiazol-5-yl)-5-methyl-thiophen-2-ylamine (75 mg, 339 μmol, Int1.8) in THF (2.5 mL) was added LiHMDS ((678 μL, 678 μmol, 1M solution in THF) at −78° C. and the resulting reaction mixture was stirred for 30 min. at −78° C. Then, 1-cyclopentene-1,2-dicarboxylic anhydride (46.8 mg, 339 μmol, CAS RN 3205-94-5) was added at −78° C. The reaction mixture was allowed to warm to 20° C. and was stirred at this temperature for 2 h. The reaction mixture was poured on 30 mL 1M aqueous HCl and 30 mL EtOAc and the layers were separated. The aqueous layer was extracted a second time with 30 mL EtOAc. The organic layers were washed with 30 mL brine, dried over MgSO$_4$, filtered and concentrated under vacuum. The product was purified by preparative HPLC (Gemini NX column) with a gradient of MeOH:H$_2$O (containing 0.1% formic acid) (80:20 to 98:2). Yellow solid (52 mg, 42.7%). MS (ESI): m/z=360.101 [M+H]$^+$.

The examples in Table 3 were prepared according to the methods used in example 6, using the 2-aminothiophene and carboxylic acid anhydride reagents as listed in Table 3, applying one of the following purification methods: Method P1: preparative HPLC, eluant MeOH:H$_2$O (containing 0.1% formic acid) (gradient 80:20 to 98:2); Method P2: MPLC, eluant CH$_2$Cl$_2$:MeOH (gradient 100:0 to 95:5); Method P3: preparative HPLC, eluant CH$_3$CN:H$_2$O (gradient 50:50 to 95:5); Method P4: preparative HPLC, eluant CH$_3$CN:H$_2$O (gradient 20:80 to 98:2); Method P5: precipitation after evaporation of organic layer.

TABLE 3

| No./ Method | Systematic name/Structure | 2-Amino-thiophene | Carboxylic acid anhydride | MS m/z |
|---|---|---|---|---|
| 6.1/P2 | 2-[3-(3-Cyclopropyl-[1,2,4]oxadiazol-5-yl)-thiophen-2-ylcarbamoyl]-cyclopent-1-enecarboxylic acid | 3-(3-Cyclopropyl-[1,2,4]oxadiazol-5-yl)-thiophen-2-amine (Int1.9) | 1-Cyclopentene-1,2-dicarboxylic anhydride (CAS RN 3205-94-5) | 346.086 [M + H]$^+$ |
| 6.2/P1 | 2-[3-(3-Cyclopropyl-[1,2,4]oxadiazol-5-yl)-4-methyl-5-oxetan-3-yl-thiophen-2-ylcarbamoyl]-cyclopent-1-enecarboxylic acid | 3-(3-Cyclopropyl-[1,2,4]oxadiazol-5-yl)-4-methyl-5-oxetan-3-yl-thiophen-2-ylamine (Int1.10) | 1-Cyclopentene-1,2-dicarboxylic anhydride (CAS RN 3205-94-5) | 416.128 [M + H]$^+$ |

TABLE 3-continued

| No./ Method | Systematic name/Structure | 2-Amino-thiophene | Carboxylic acid anhydride | MS m/z |
| --- | --- | --- | --- | --- |
| 6.3/P1 | 2-[3-(3-Cyclopropyl-[1,2,4]oxadiazol-5-yl)-4-methyl-5-oxetan-3-yl-thiophen-2-ylcarbamoyl]-cyclohex-1-enecarboxylic acid | 3-(3-Cyclopropyl-[1,2,4]oxadiazol-5-yl)-4-methyl-5-oxetan-3-yl-thiophen-2-ylamine (Int1.10) | 1-Cyclohexene-1,2-dicarboxylic anhydride (CAS RN 2426-02-0) | 430.143 [M + H]⁺ |
| 6.4/P3 | 2-[3-(3-Cyclopropyl-[1,2,4]oxadiazol-5-yl)-5-methyl-4-trifluoromethyl-thiophen-2-ylcarbamoyl]-cyclopent-1-enecarboxylic acid | 3-(3-Cyclopropyl-[1,2,4]oxadiazol-5-yl)-5-methyl-4-trifluoromethyl-thiophen-2-ylamine (Int1.11) | 1-Cyclopentene-1,2-dicarboxylic anhydride (CAS RN 3205-94-5) | 428.087 [M + H]⁺ |
| 6.5/P1 | 5-[(2-Carboxy-cyclopent-1-enecarbonyl)-amino]-4-(3-cyclopropyl-[1,2,4]oxadiazol-5-yl)-3- | 5-Amino-4-(3-cyclopropyl-[1,2,4]oxadiazol-5-yl)-3-methyl- | 1-Cyclopentene-1,2-dicarboxylic anhydride (CAS RN 3205-94-5) | 432.12 [M + H]⁺ |

The MS m/z values shown correspond to [M + H]⁺ ions.

TABLE 3-continued

| No./Method | Systematic name/Structure | 2-Amino-thiophene | Carboxylic acid anhydride | MS m/z |
|---|---|---|---|---|
| | methyl-thiophene-2-carboxylic acid ethyl ester | thiophene-2-carboxylic acid ethyl ester (Int1.12) | | |
| 6.6/P3 | 2-[3-(3-Cyclopropyl-[1,2,4]oxadiazol-5-yl)-5-dimethylcarbamoyl-4-methyl-thiophen-2-ylcarbamoyl]-cyclopent-1-enecarboxylic acid | 5-Amino-4-(3-cyclopropyl-[1,2,4]oxadiazol-5-yl)-3-methyl-thiophene-2-carboxylic acid dimethylamide (Int1.13) | 1-Cyclopentene-1,2-dicarboxylic anhydride (CAS RN 3205-94-5) | 431.139 [M + H]⁺ |
| 6.7/P4 | 2-[5-Cyclopropyl-3-(3-cyclopropyl-[1,2,4]oxadiazol-5-yl)-thiophen-2-ylcarbamoyl]-cyclopent-1-enecarboxylic acid | 5-Cyclopropyl-3-(3-cyclopropyl-[1,2,4]oxadiazol-5-yl)-thiophen-2-ylamine (Int1.14) | 1-Cyclopentene-1,2-dicarboxylic anhydride (CAS RN 3205-94-5) | 386.117 [M + H]⁺ |
| 6.8/P4 | 2-[4-Cyclopropyl-3-(3-cyclopropyl-[1,2,4]oxadiazol-5-yl)-thiophen-2-ylcarbamoyl]-cyclopent-1-enecarboxylic acid | 4-Cyclopropyl-3-(3-cyclopropyl-[1,2,4]oxadiazol-5-yl)-thiophen-2-ylamine (Int1.15) | 1-Cyclopentene-1,2-dicarboxylic anhydride (CAS RN 3205-94-5) | 386.117 [M + H]⁺ |

TABLE 3-continued

| No./Method | Systematic name/Structure | 2-Amino-thiophene | Carboxylic acid anhydride | MS m/z |
|---|---|---|---|---|
| 6.9/P4 | 2-[3-(3-Cyclopropyl-[1,2,4]oxadiazol-5-yl)-4-methyl-thiophen-2-ylcarbamoyl]-cyclopent-1-enecarboxylic acid | 3-(3-Cyclopropyl-[1,2,4]oxadiazol-5-yl)-4-methyl-thiophen-2-ylamine (Int1.16) | 1-Cyclopentene-1,2-dicarboxylic anhydride (CAS RN 3205-94-5) | 360.101 [M + H]⁺ |
| 6.10/P4 | 2-[3-(3-Cyclopropyl-[1,2,4]oxadiazol-5-yl)-5-(2,2,2-trifluoro-ethyl)-thiophen-2-ylcarbamoyl]-cyclopent-1-enecarboxylic acid | 3-(3-Cyclopropyl-[1,2,4]oxadiazol-5-yl)-5-(2,2,2-trifluoro-ethyl)-thiophen-2-ylamine (Int1.17) | 1-Cyclopentene-1,2-dicarboxylic anhydride (CAS RN 3205-94-5) | 428.088 [M + H]⁺ |
| 6.11/P4 | 2-[3-(3-Cyclopropyl-[1,2,4]oxadiazol-5-yl)-4-trifluoromethyl-thiophen-2-ylcarbamoyl]-cyclopent-1-enecarboxylic acid | 3-(3-Cyclopropyl-[1,2,4]oxadiazol-5-yl)-4-trifluoromethyl-thiophen-2-ylamine | 1-Cyclopentene-1,2-dicarboxylic anhydride (CAS RN 3205-94-5) | 414.072 [M + H]⁺ |

TABLE 3-continued

| No./Method | Systematic name/Structure | 2-Aminothiophene | Carboxylic acid anhydride | MS m/z |
|---|---|---|---|---|
| | 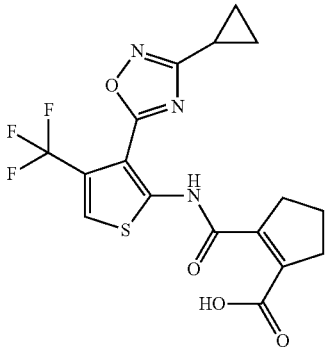 [SMILES: O=C(O)C1=C(C(=O)Nc2scc(C(F)(F)F)c2-c2nc(C3CC3)no2)CCC1] (Int1.18) | | | |
| 6.12/P6 | 2-[3-(3-Cyclopropyl-[1,2,4]oxadiazol-5-yl)-5-(5-dimethylamino-[1,2,4]thiadiazol-3-yl)-4-methyl-thiophen-2-ylcarbamoyl]-cyclopent-1-enecarboxylic acid 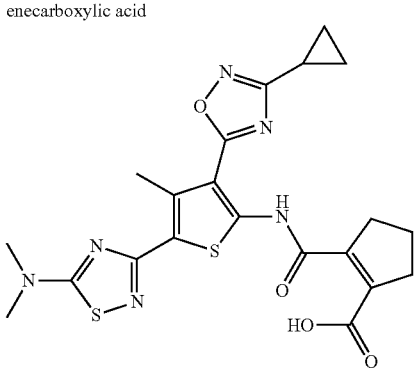 | {3-[5-Amino-4-(3-cyclopropyl-[1,2,4]oxadiazol-5-yl)-3-methyl-thiophen-2-yl]-[1,2,4]thiadiazol-5-yl}-dimethyl-amine (Int1.19) | 1-Cyclopentene-1,2-dicarboxylic anhydride (CAS RN 3205-94-5) | 487.122 [M + H]+ |

Intermediates

General Procedure A: Preparation of 2-Aminothiophene

Method A1: Cleavage of Boc-Protected 2-Aminothiophene

The Boc-protected 2-aminothiophene (0.5 mmol) is dissolved in dioxane (5% solution) and 4M HCl in dioxane (10 mmol) is added. The solution is stirred at RT until TLC indicates completion of the reaction. The crude reaction mixture is concentrated in vacuo to give the desired compound which is used in the next step without further purification.

Method A2: One-Pot Gewald Reaction

To the solution of the aldehyde or ketone (5 mmol) in MeOH (5% solution) the heterocyclic acetonitrile derivative (5 mmol), morpholine (12.5 mmol) and elemental sulfur (5.5 mmol) are added and the reaction mixture stirred at 65° C. overnight. After cooling to room temperature the reaction mixture is extracted with EtOAc and half saturated NH$_4$Cl solution. The organic layer is dried over Na$_2$SO$_4$ and activated carbon, evaporated and the compound purified by silica gel chromatography on a 50 g column using a gradient of n-heptane: EtOAc as eluant.

Method A3: Ring Closure of Knoevenagel Adduct

To a solution of the Knoevenagel adduct (1.5 mmol) in EtOH (20 mL) is added DBU (3.75 mmol) and sulfur (1.5 mmol). The reaction mixture is stirred at 65° C. for 2 h and then poured on 10% aqueous NaHCO$_3$ solution (30 mL) and EtOAc (30 mL). The layers are separated and the aqueous layer extracted a second time with EtOAc (30 mL). The organic layers are washed with 30 mL brine, dried over MgSO$_4$, filtered and concentrated under vacuum. The compound is purified by silica gel chromatography on a 20 g column using an MPLC system (CombiFlash Companion, Isco Inc.) eluting with a gradient of n-heptane: EtOAc.

Method A4: Ester to Oxadiazole Conversion on 2-Aminothiophene

To the solution of the 3-(methyl or ethyl)ester-substituted 2-amino thiophene (3.0 mmol) in EtOH (5 mL) N-hydroxyalkyl- or -cycloalkyl-carboximidamide (3.0 mmol) and NaOEt solution (21 wt % solution in EtOH, 3.0 mmol) are added and the reaction mixture stirred at 70° C. until completion of the reaction as indicated by TLC or LC-MS. Depending on the progress of the reaction another batch of N-hydroxycyclopropanecarboximidamide and sodium ethoxide solution might be added. The reaction mixture is poured on 30 mL 10% aqueous NaHCO$_3$ solution and 30 mL EtOAc and the layers are separated. The aqueous layer is extracted a second time with 30 mL EtOAc and the organic layers are washed with 30 mL brine, dried over MgSO$_4$, filtered and concentrated under vacuum. The product is purified by preparative HPLC (Gemini NX column) with a gradient of MeOH: H$_2$O (containing 0.1% formic acid).

Method A5: Ester to Oxadiazole Conversion on 2-Aminothiophene Using Microwave

To a solution of the 3-(methyl or ethyl)ester-substituted 2-amino thiophene (2 mmol) in EtOH (4 mL) is added N-hydroxy-alkyl- or -cycloalkyl-carboximidamide (2 mmol) and NaOEt (21 wt % solution in EtOH (2 mmol). Microwave heating (120° C.) is applied to the reaction mixture until LC-MS indicates completion of conversion (typically 30 min.). The reaction mixture is poured on 30 mL 10% aqueous NaHCO₃ solution and 30 mL EtOAc and the layers are separated. The aqueous layer is extracted a second time with 30 mL EtOAc and the organic layers are washed with 30 mL brine, dried over MgSO₄, filtered and concentrated under vacuum. The compound is purified by silica gel chromatography on a 20 g column using an MPLC (Flashmaster) system eluting with a gradient of n-heptane:EtOAc (100:0 to 60:40).
Method A6: One-Pot Gewald Reaction Using Microwave Conditions To the solution of the aldehyde or keton (1 mmol) in EtOH (1.5 mL) the heterocyclic acetonitrile derivative (1 mmol), sulfur (1 mmol) and N-methylmorpholine (1 mmol) are added, the reaction mixture heated in a microwave oven at 120-150° C. for 30 min. and then poured on 30 mL 10% aqueous NaHCO₃ solution and 30 mL EtOAc and the layers are separated. The aqueous layer is extracted a second time with 30 mL EtOAc. The organic layers are washed with 30 mL brine, dried over MgSO₄, filtered and evaporated. The compound is purified by silica gel chromatography on a 20 g column using an MPLC system (CombiFlash Companion, Isco Inc.) eluting with a gradient of n-heptane:EtOAc.
Method A7: Modified One-Pot Gewald Reaction To a solution of the aldehyde or ketone (3 mmol) in EtOH (7 mL) are added the heterocyclic acetonitrile derivative (3 mmol) and elemental sulfur (3 mmol) and the reaction mixture is stirred at 50° C. for 30 min. Then, morpholine (180 mmol) is added dropwise over 10 min. The reaction mixture is stirred at 50° C. for 1.5 h and then poured on 30 mL 10% aqueous NaHCO₃ solution and 30 mL EtOAc and the layers are separated. The aqueous layer is extracted a second time with 30 mL EtOAc and the organic layers are washed with 30 mL brine, dried over MgSO₄, filtered and concentrated under vacuum. The compound is purified by silica gel chromatography on a 20 g column using an MPLC system (CombiFlash Companion, Isco Inc.) eluting with a gradient of n-heptane: EtOAc.

The intermediates in Table 4 were prepared according to the methods described above and using the starting material as listed in Table 4:

TABLE 4

| No. | Method | Systematic name/ Structure | Starting material(s) | MS m/z |
| --- | --- | --- | --- | --- |
| Int1.1 | A1 | 3-Phenyl-thiophen-2-ylamine 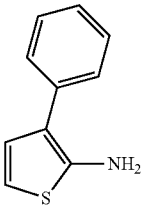 [SMILES: Nc1sccc1-c1ccccc1] | (3-Phenyl-thiophen-2-yl)-carbamic acid tert-butyl ester (intermediate 4) | 176.0 [M + H]⁺ |
| Int1.2 | A2 | Methyl 5-amino-3-methyl-4-(4-methylthiazol-2-yl)thiophene-2-carboxylate 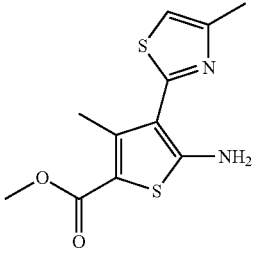 | Methyl acetoacetate (CAS RN 105-45-3); 2-(4-Methylthiazol-2-yl)acetonitrile (CAS RN 19785-39-8) | 269.04 [M + H]⁺ |
| Int1.3 | A3 | 4-Cyclopropyl-5-methyl-3-(3-methyl-[1,2,4]oxadiazol-5-yl)-thiophen-2-ylamine 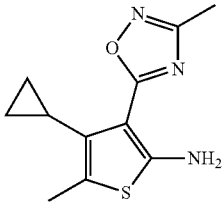 [SMILES: Cc1noc(-c2c(N)sc(C)c2C2CC2)n1] | (E/Z)-3-Cyclopropyl-2-(3-methyl-[1,2,4]oxadiazol-5-yl)-pent-2-enenitrile (Int2.1) | 236.086 [M + H]⁺ |

TABLE 4-continued

| No. | Method | Systematic name/ Structure | Starting material(s) | MS m/z |
|---|---|---|---|---|
| Int1.4 | A3 | 4-Cyclopropyl-5-methyl-3-(3-trifluoromethyl-[1,2,4]oxadiazol-5-yl)-thiophen-2-ylamine | (E/Z)-3-Cyclopropyl-2-(3-trifluoromethyl-[1,2,4]oxadiazol-5-yl)-pent-2-enenitrile (Int2.3) | 289 [M]$^+$ |
| Int1.5 | A3 | 3-(3-Cyclopropyl-[1,2,4]oxadiazol-5-yl)-4,5-dimethyl-thiophen-2-ylamine | (E/Z)-2-(3-Cyclopropyl-[1,2,4]oxadiazol-5-yl)-3-methyl-pent-2-enenitrile (Int2.4) | 236.086 [M + H]$^+$ |
| Int1.6 | A3 | 5-Cyclopropyl-3-(3-cyclopropyl-[1,2,4]oxadiazol-5-yl)-4-methyl-thiophen-2-ylamine | (E/Z)-4-Cyclopropyl-2-(3-cyclopropyl-[1,2,4]oxadiazol-5-yl)-3-methyl-but-2-enenitrile (Int2.5) | 262.101 [M + H]$^+$ |
| Int1.7 | A3 | 4-Cyclopropyl-3-(3-cyclopropyl-[1,2,4]oxadiazol-5-yl)-5-methyl-thiophen-2-ylamine | (E/Z)-3-Cyclopropyl-2-(3-cyclopropyl-[1,2,4]oxadiazol-5-yl)-pent-2-enenitrile (Int2.2) | 262.102 [M + H]$^+$ |
| Int1.8 | A4 | 3-(3-Cyclopropyl-[1,2,4]oxadiazol-5-yl)-5-methyl-thiophen-2-ylamine | Methyl 2-amino-5-methylthiophene-3-carboxylate (CAS RN 19369-53-0) | 222.070 [M + H]$^+$ |

TABLE 4-continued

| No. | Method | Systematic name/ Structure | Starting material(s) | MS m/z |
|---|---|---|---|---|
| | | 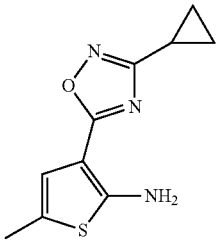 | N'-hydroxycyclopropane-carboximidamide (CAS RN 51285-13-3) | |
| Int1.9 | A4 | 3-(3-Cyclopropyl-[1,2,4]oxadiazol-5-yl)-thiophen-2-amine<br>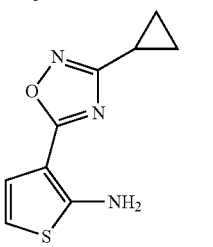 | Methyl 2-aminothiophene-3-carboxylate (CAS RN 4651-81-4)<br>N'-hydroxycyclopropane-carboximidamide (CAS RN 51285-13-3) | 208.054 [M + H]⁺ |
| Int1.10 | A3 | 3-(3-Cyclopropyl-[1,2,4]oxadiazol-5-yl)-4-methyl-5-oxetan-3-yl-thiophen-2-ylamine<br>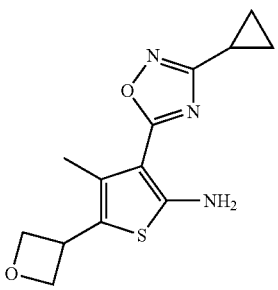 [SMILES: Cc1c(C2COC2)sc(N)c1-c1nc(C2CC2)no1] | (E/Z)-3-Methyl-2-(3-methyl-[1,2,4]oxadiazol-5-yl)-4-oxetan-3-yl-but-2-enenitrile (Int2.6) | 278.096 [M + H]⁺ |
| Int1.11 | A6 | 3-(3-Cyclopropyl-[1,2,4]oxadiazol-5-yl)-5-methyl-4-trifluoromethyl-thiophen-2-ylamine<br>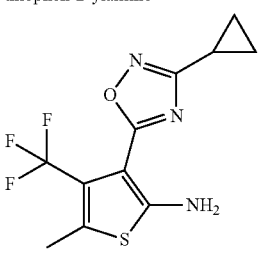 | 1,1,1-Trifluorobutan-2-one (CAS RN 381-88-4)<br>(3-Cyclopropyl-1,2,4-oxadiazol-5-yl)acetonitrile (Int3.2) | 290.057 [M + H]⁺ |
| Int1.12 | A7 | 5-Amino-4-(3-cyclopropyl-[1,2,4]oxadiazol-5-yl)-3-methyl-thiophene-2-carboxylic acid ethyl ester | Methyl acetoacetate (CAS RN 105-45-3)<br>(3-Cyclopropyl-1,2,4-oxadiazol-5-yl)acetonitrile (Int3.2) | 294.090 [M + H]⁺ |

TABLE 4-continued

| No. | Method | Systematic name/ Structure | Starting material(s) | MS m/z |
|---|---|---|---|---|
| | | 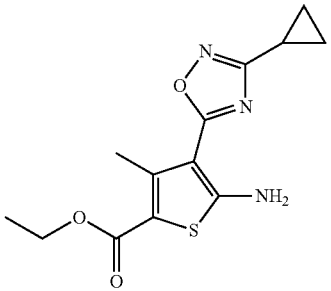 [SMILES: CCOC(=O)c1sc(N)c(-c2nc(C3CC3)no2)c1C] | | |
| Int1.13 | A7 | 5-Amino-4-(3-cyclopropyl-[1,2,4]oxadiazol-5-yl)-3-methyl-thiophene-2-carboxylic acid dimethylamide 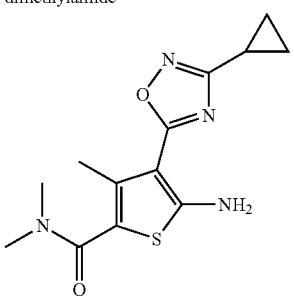 | N,N-dimethyl-3-oxobutanamide (70 wt % in H$_2$O; CAS RN 2044-64-6) (3-Cyclopropyl-1,2,4-oxadiazol-5-yl)acetonitrile (Int3.2) | 293.107 [M + H]$^+$ |
| Int1.14 | A6 | 5-Cyclopropyl-3-(3-cyclopropyl-[1,2,4]oxadiazol-5-yl)-thiophen-2-ylamine 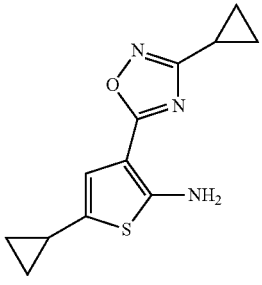 [SMILES: Nc1sc(C2CC2)cc1-c1nc(C2CC2)no1] | Cyclopropylacetaldehyde (CAS RN 56105-19-2) (3-Cyclopropyl-1,2,4-oxadiazol-5-yl)acetonitrile (Int3.2) | 248.085 [M + H]$^+$ |
| Int1.15 | A6 | 4-Cyclopropyl-3-(3-cyclopropyl-[1,2,4]oxadiazol-5-yl)-thiophen-2-ylamine 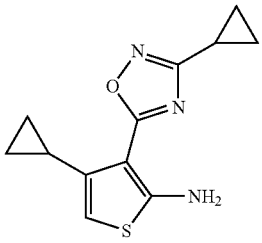 [SMILES: Nc1scc(C2CC2)c1-c1nc(C2CC2)no1] | Cyclopropyl methyl ketone (CAS RN 765-43-5) (3-Cyclopropyl-1,2,4-oxadiazol-5-yl)acetonitrile (Int3.2) | 248.086 [M + H]$^+$ |
| Int1.16 | A5 | 3-(3-Cyclopropyl-[1,2,4]oxadiazol-5-yl)-4-methyl-thiophen-2-ylamine | 2-Amino-4-methyl-thiophene-3-carboxylic acid ethyl ester (CAS RN 43088-42-2) | 222.070 [M + H]$^+$ |

TABLE 4-continued

| No. | Method | Systematic name/ Structure | Starting material(s) | MS m/z |
|---|---|---|---|---|
| | | 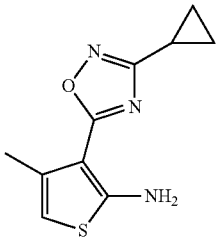 | N'-hydroxycyclopropane-carboximidamide (CAS RN 51285-13-3) | |
| Int1.17 | A6 | 3-(3-Cyclopropyl-[1,2,4]oxadiazol-5-yl)-5-(2,2,2-trifluoro-ethyl)-thiophen-2-ylamine 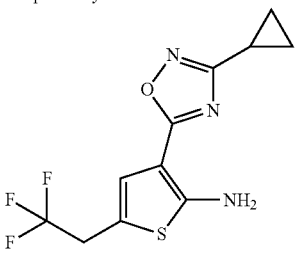 | 4,4,4-Trifluorobutanal (CAS RN 406-87-1) (3-Cyclopropyl-1,2,4-oxadiazol-5-yl)acetonitrile (Int3.2) | 290.057 [M + H]⁺ |
| Int1.18 | A6 | Intermediate 3-(3-Cyclopropyl-[1,2,4]oxadiazol-5-yl)-4-trifluoromethyl-thiophen-2-ylamine 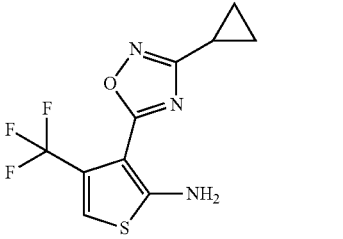 [SMILES: Nc1scc(C(F)(F)F)c1-c1nc(C2CC2)no1] | 1,1,1-Trifluoropropan-2-one (CAS RN 421-50-1) (3-Cyclopropyl-1,2,4-oxadiazol-5-yl)acetonitrile (Int3.2) | 276.042 [M + H]⁺ |
| Int1.19 | A6 | {3-[5-Amino-4-(3-cyclopropyl-[1,2,4]oxadiazol-5-yl)-3-methyl-thiophen-2-yl]-[1,2,4]thiadiazol-5-yl}-dimethyl-amine 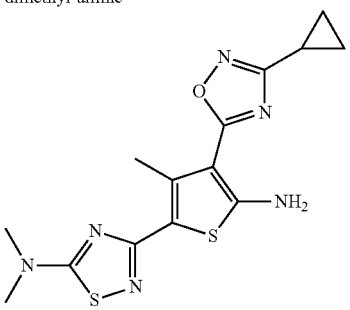 | 1-(5-Dimethylamino-[1,2,4]thiadiazol-3-yl)-propan-2-one (3-Cyclopropyl-1,2,4-oxadiazol-5-yl)acetonitrile (Int3.2) | 349.091 [M + H]⁺ |

General Procedure B: Preparation of Knoevenagel Adducts

Method B1:

To a suspension of the ketone or aldehyde (3 mmol) in toluene (9 mL) the heterocyclyl-acetonitrile and NH₄OAc (6 mmol) are added. The reaction mixture is stirred at 100° C. for 18 h, then poured on 10% aqueous NaHCO₃ solution (30 mL) and EtOAc (30 mL) and the layers are separated. The aqueous layer is extracted a second time with EtOAc (30 mL) and the organic layers are washed with brine (30 mL), dried over MgSO₄, filtered and concentrated under vacuum. The compound is purified by silica gel chromatography on a 20 g column using an MPLC (Flashmaster) system eluting with a gradient of n-heptane:EtOAc.

The intermediates in Table 5 were prepared according to the methods described above and using the starting materials as listed in Table 5:

TABLE 5

| No. | Method | Systematic name/ Structure | Starting material | MS m/z |
|---|---|---|---|---|
| Int2.1 | B1 | (E/Z)-3-Cyclopropyl-2-(3-methyl-[1,2,4]oxadiazol-5-yl)-pent-2-enenitrile | 1-Cyclopropylpropan-1-one (CAS RN 6704-19-4) (3-Methyl-[1,2,4]oxadiazol-5-yl)-acetonitrile (Int3.1) | 203 [M]$^+$ |
| Int2.2 | B1 | (E/Z)-3-Cyclopropyl-2-(3-cyclopropyl-[1,2,4]oxadiazol-5-yl)-pent-2-enenitrile | 1-Cyclopropyl-propan-1-one (CAS RN 6704-19-4) (3-Cyclopropyl-[1,2,4]oxadiazol-5-yl)-acetonitrile (Int3.2) | 229 [M]$^+$ |
| Int2.3 | B1 | (E/Z)-3-Cyclopropyl-2-(3-trifluoromethyl-[1,2,4]oxadiazol-5-yl)-pent-2-enenitrile | 1-Cyclopropyl-propan-1-one (CAS RN 6704-19-4) (3-Trifluoromethyl-[1,2,4]oxadiazol-5-yl)-acetonitrile (Int3.3) | 257 [M + H]$^+$ |
| Int2.4 | B1 | (E/Z)-2-(3-Cyclopropyl-[1,2,4]oxadiazol-5-yl)-3-methyl-pent-2-enenitrile | Butan-2-one (CAS RN 78-93-3) (3-Cyclopropyl-[1,2,4]oxadiazol-5-yl)-acetonitrile (Int3.2) | 202.099 [M − H]$^-$ |

TABLE 5-continued

| No. | Method | Systematic name/ Structure | Starting material | MS m/z |
|---|---|---|---|---|
| Int2.5 | B1 | (E/Z)-4-Cyclopropyl-2-(3-cyclopropyl-[1,2,4]oxadiazol-5-yl)-3-methyl-but-2-enenitrile | 1-Cyclopropyl-propan-2-one (CAS RN 4160-75-3-Cyclopropyl-[1,2,4]oxadiazol-5-yl)-acetonitrile (Int3.2) | 229 [M]$^+$ |
| Int2.6 | B1 | (E/Z)-3-Methyl-2-(3-methyl-[1,2,4]oxadiazol-5-yl)-4-oxetan-3-yl-but-2-enenitrile | 1-(Oxetan-3-yl)propan-2-one (CAS RN 1207175-39-0) (3-Cyclopropyl-1,2,4-oxadiazol-5-yl)acetonitrile (Int3.2) | 246.124 [M + H]$^+$ |

General Procedure C: Preparation of Cyanomethyl-Oxadiazoles

Method C1:

To a solution of the N-hydroxy-alkyl- or -cycloalkyl-carboximidamide (50 mmol) in dioxane (150 mL) is added 3-(3,5-dimethyl-1H-pyrazol-1-yl)-3-oxopropanenitrile (55 mmol). The reaction mixture is stirred at reflux temperature for 3 h and then concentrated under vacuum. The compound is purified by silica gel chromatography on a 330 g column using a MPLC system (CombiFlash Companion XL, Isco Inc.) eluting with a gradient of n-heptane:EtOAc.

Method C2:

To a suspension of NaCN (30 mmol) in CH$_3$CN (10 mL) is added 15-crown-5 (10 mmol, CAS RN 33100-27-5) and the suspension is stirred at RT for 45 min. To this mixture is added dropwise a solution of the 5-(chloromethyl)-3-substituted 1,2,4-oxadiazole (5 mmol) in CH$_3$CN (5 mL) over 30 min. The light yellow suspension is stirred at RT for 3 h and then poured on 100 mL H$_2$O and 100 mL EtOAc and the layers are separated. The aqueous layer is extracted a second time with 100 mL EtOAc and the organic layers are washed with 100 mL brine, dried over MgSO$_4$, filtered and concentrated under vacuum. The compound is purified by silica gel chromatography on a 50 g column using a MPLC system (CombiFlash Companion, Isco Inc.) eluting with a gradient of n-heptane:EtOAc.

The intermediates in Table 6 were prepared according to the methods described above and using the starting materials as listed in Table 6.

TABLE 6

| No. | Method | Systematic name/ Structure | Starting material(s) | MS m/z |
|---|---|---|---|---|
| Int3.1 | C1 | (3-Methyl-[1,2,4]oxadiazol-5-yl)-acetonitrile | N'-hydroxy-acetimidamide (CAS RN 22059-22-9) 3-(3,5-Dimethyl-1H-pyrazol-1-yl)-3-oxopropanenitrile (CAS RN 36140-83-7) | 123 [M]$^+$ |
| Int3.2 | C1 | (3-Cyclopropyl-[1,2,4]oxadiazol-5-yl)-acetonitrile | N'-hydroxycyclo-propane-carbox-imidamide (CAS RN 51285-13-3) 3-(3,5-dimethyl-1H-pyrazol-1-yl)-3-oxopropane-nitrile (CAS RN 36140-83-7) | 148.052 [M − H]$^-$ |

TABLE 6-continued

| No. | Method | Systematic name/ Structure | Starting material(s) | MS m/z |
|---|---|---|---|---|
| Int3.3 | C2 | (3-Trifluoromethyl-[1,2,4]oxadiazol-5-yl)-acetonitrile 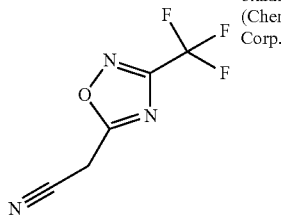 | 5-(Chloromethyl)-3-(trifluoromethyl)-1,2,4-oxadiazole (ChemBridge Corp.) | 177 [M]+ |

Intermediate 4

(3-Phenyl-thiophen-2-yl)-carbamic acid tert-butyl ester

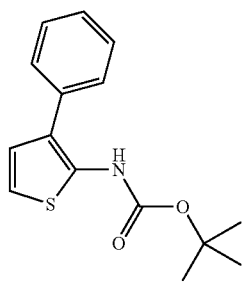 [SMILES: CC(C)(C)OC(=O)Nc1sccc1-c1ccccc1]

3-Phenyl-thiophene-2-carboxylic acid (200 mg, 979 µmol), NEt₃ (99.1 mg, 136 µL, 979 µmol) and diphenylphosphoryl azide (275 mg, 215 µL, 999 µmol) were dissolved in tert-BuOH. The solution was stirred at 85° C. for 5 h followed by RT overnight. The formed suspension was filtered and the filter cake was washed with a small amount of tert-BuOH. The filtrate was diluted with EtOAc, washed with H₂O and brine. The organic layers were dried over Na₂SO₄ and concentrated in vacuo. The crude material was purified by flash chromatography (0% to 18% EtOAc in n-heptane) to give the title compound as a yellow solid (0.122 g, 45%). MS (ESI): m/z=276.2 [M+H]+.

Intermediate 5

3-Phenyl-thiophene-2-carboxylic acid

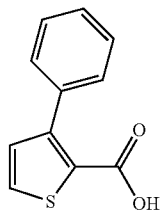 [SMILES: O=C(O)c1sccc1-c1ccccc1]

3-Phenyl-thiophene-2-carbaldehyde (0.527 g, 2.8 mmol) was diluted in CH₃CN (12.4 mL) and the solution was cooled to 10° C. A solution of NaH₂PO₄ (47 mg, 0.392 mmol) in H₂O (0.54 mL) and of hydrogen peroxide (1.36 g, 1.2 mL, 14.0 mmol, 35% wt solution in water) was added followed by a solution of NaClO₂ (0.166 g, 1.83 mmol) in H₂O (1.89 mL) over 5 min. The resulting two phase system was vigorously stirred at 10° C. for 2 h. Stirring was continued at RT overnight. The reaction was quenched by cooling to 10° C. and by addition of Na₂SO₃. Then the reaction mixture was poured onto an aqueous solution of Na₂SO₃. A clear two phase system was generated by adding some H₂O. After acidification to pH 1 with 5M aqueous HCl a suspension formed which was filtered. The solid was washed with H₂O and dried under high vacuum to give the title compound as a white solid (0.532 g, 92%). MS (ESI): m/z=203.1 [M−H]−.

Intermediate 6

3-Phenyl-thiophene-2-carbaldehyde

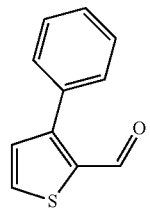 [SMILES: O=Cc1sccc1-c1ccccc1]

3-Bromothiophene-2-carbaldehyde (3 g, 1.67 ml, 14.8 mmol, CAS RN 930-96-1) was dissolved in DME (180 mL) and the resulting solution was evacuated and purged with argon three times. Pd(Ph₃P)₄ (512 mg, 443 µmol) was added, the reaction flask purged again with argon and stirring was continued at RT for 15 min. Then 2M aqueous Na₂CO₃ solution was added (14.8 mL, 29.5 mmol) followed by phenylboronic acid (1.98 g, 16.2 mmol). Again the reaction flask was purged with argon and the reaction mixture was heated to 80° C. and stirred for 6.5 h. After evaporation of the solvent, the residue was taken up in Et₂O and H₂O and the layers were separated. The organic layer was dried over Na₂SO₄, filtered and evaporated. The crude residue was suspended in CH₂Cl₂ and n-heptane and the solid was filtered off. The filtrate was evaporated and the crude product purified by flash chromatography on silica gel (gradient EtOAc/n-heptane, 0% to 10%). The product-containing fractions were pooled and further purified by preparative HPLC to give the title compound as a yellow oil (0.939 g, 34%). MS (ESI): m/z=189.2 [M+H]+.

Intermediate 7

2-[4-Cyclopropyl-5-methyl-3-(3-trifluoromethyl-[1,2,4]oxadiazol-5-yl)-thiophen-2-ylcarbamoyl]-cyclopent-1-enecarboxylic acid methyl ester

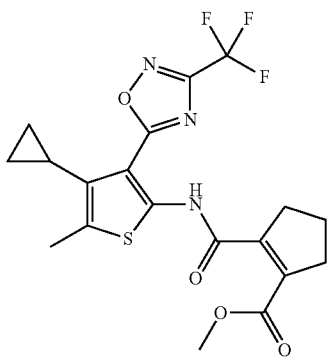 [SMILES: COC(=O)C1=C(C(=O)Nc2sc(C)c(C3CC3)c2-c2nc(C(F)(F)F)no2)CCC1]

To cyclopent-1-ene-1,2-dicarboxylic acid monomethyl ester (50.0 mg, 294 µmol, prepared in analogy to T. Yoshimutsu, T. Tanaka et al., *Heterocycles* 2009, 77(1), 179-186) was added DMF (2.15 mg, 2.28 µl, 29.4 µmol) and thionyl chloride (699 mg, 429 µl, 5.88 mmol) and the solution was heated to reflux for 30 min. The reaction mixture was concentrated under vacuum and the residue was diluted three times with toluene followed by evaporation to completely remove thionyl chloride. The residue was dissolved in $CH_2Cl_2$ (2 mL) and the solution was added to a solution of 4-cyclopropyl-5-methyl-3-(3-trifluoromethyl-[1,2,4]oxadiazol-5-yl)-thiophen-2-ylamine (85 mg, 294 µmol, Int1.4) and DIPEA (76.0 mg, 103 µl, 588 µmol) in $CH_2Cl_2$ (3 mL) and the light brown solution was stirred at RT for 18 h. The reaction mixture was poured on 30 mL 10% aqueous $NaHCO_3$ solution and 30 mL EtOAc and the layers were separated. The aqueous layer was extracted a second time with 30 mL EtOAc. The organic layers were washed with 30 mL brine, dried over $MgSO_4$, filtered and concentrated under vacuum. The compound was purified by silica gel chromatography on a 20 g column using an MPLC (Flashmaster) system eluting with a gradient of n-heptane:EtOAc (100:0 to 75:25). Light yellow solid (88 mg, 67.8%). MS (ESI): m/z=442.104 [M+H]+.

The intermediates in Table 7 were prepared according to the method described under intermediate 7 and using the starting materials as listed in Table 7.

TABLE 7

| No. | Systematic name/ Structure | 2-Amino-thiophene | Carboxylic acid | MS m/z |
|---|---|---|---|---|
| Int. 7.1 | Ethyl 4-[[3-(3-cyclopropyl-1,2,4-oxadiazol-5-yl)-4,5-dimethyl-2-thienyl]carbamoyl]-3,6-dihydro-2H-pyran-5-carboxylate | 3-(3-Cyclopropyl-1,2,4-oxadiazol-5-yl)-4,5-dimethylthiophen-2-amine (Int1.5) | 4-(Ethoxy-carbonyl)-5,6-dihydro-2H-pyran-3-carboxylic acid (Intermediate 8) | 418.14 [M + H]+ |

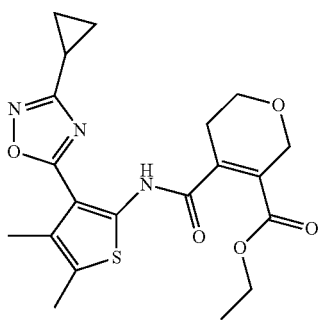 [SMILES: CCOC(=O)C1=C(C(=O)Nc2sc(C)c(C)c2-c2nc(C3CC3)no2)CCOC1]

Example 7 trans-2-[3-(3-Cyclopropyl-[1,2,4]oxadiazol-5-yl)-4,5-dimethyl-thiophen-2-ylcarbamoyl]-cyclohexanecarboxylic acid

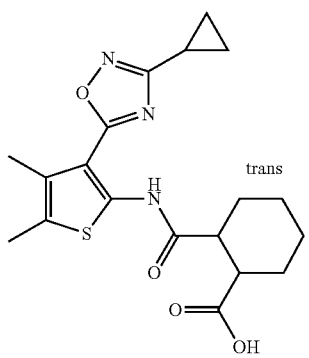 [SMILES: Cc1sc(NC(=O)C2CCCCC2C(=O)O)c(-c2nc(C3CC3)no2)c1C]

To a solution of 3-(3-cyclopropyl-1,2,4-oxadiazol-5-yl)-4,5-dimethylthiophen-2-amine (0.08 g, 340 μmol, Int1.5) in tert-butyl methyl ether (2 mL) was added trans 1,2-cyclohexanedicarboxylic anhydride (62.9 mg, 408 μmol, CAS RN 14166-21-3) and the clear solution was heated to reflux for 19 h. The reaction mixture was evaporated and the product purified by preparative HPLC (Gemini NX column) using a gradient of MeOH:H$_2$O (containing 0.1% formic acid) (20:80 to 98:2). Colorless solid (0.1 g; 75.5%). MS (ESI): m/z=390.15 [M+H]$^+$.

The examples in Table 8 were prepared according to the methods used in example 7, using the 2-aminothiophene and carboxylic acid derivative reagents as listed in Table 8.

Examples 8 and 9

5-[3-(3-Cyclopropyl-[1,2,4]oxadiazol-5-yl)-4,5-dimethyl-thiophen-2-ylcarbamoyl]-3,6-dihydro-2H-pyran-4-carboxylic acid and 4-[3-(3-Cyclopropyl-[1,2,4]oxadiazol-5-yl)-4,5-dimethyl-thiophen-2-ylcarbamoyl]-5,6-dihydro-2H-pyran-3-carboxylic acid

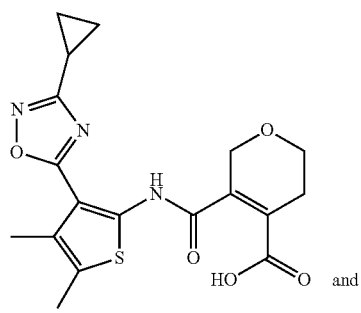

and

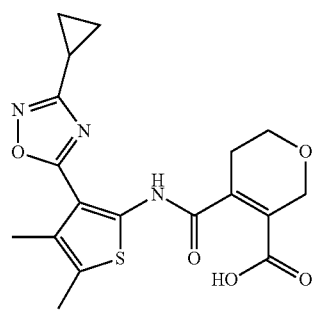

TABLE 8

| No. | Systematic name/Structure | 2-Aminothiophene | Carboxylic acid anhydride | MS m/z |
|---|---|---|---|---|
| 7.1 | cis-2-[3-(3-Cyclopropyl-[1,2,4]oxadiazol-5-yl)-4,5-dimethyl-thiophen-2-ylcarbamoyl]-cyclohexanecarboxylic acid | 3-(3-Cyclopropyl-1,2,4-oxadiazol-5-yl)-4,5-dimethylthiophen-2-amine (Int1.5) | Cis 1,2-cyclohexanedicarboxylic anhydride (CAS RN 13149-00-3) | 390.15 [M + H]$^+$ |

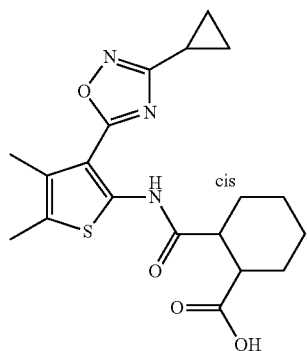 [SMILES: Cc1sc(NC(=O)C2CCCCC2C(=O)O)c(-c2nc(C3CC3)no2)c1C]

To a suspension of ethyl 5-(3-(3-cyclopropyl-1,2,4-oxadiazol-5-yl)-4,5-dimethylthiophen-2-ylcarbamoyl)-3,6-dihydro-2H-pyran-4-carboxylate (272 mg, 652 µmol, Int7.1) in dioxane (3 mL) and H₂O (3 mL) was added LiOH monohydrate (15.6 mg, 652 µmol) and the reaction mixture was stirred at room temperature for 6 h. Then another batch of LiOH monohydrate (7.8 mg, 326 µmol) was added. The thick yellow suspension was evaporated. The residue was suspended in H₂O (approx. 3.5 mL) and treated with 1M aqueous HCl (3 mL). This mixture was extracted twice with EtOAc. The organic layers were once washed with brine, dried over MgSO₄, filtered and evaporated. The residue was purified by two silica gel chromatographies on a 50 g column using an MPLC system (CombiFlash Companion XL, Isco Inc.) eluting with a gradient of CH₂Cl₂:MeOH (100:0 to 90:10). Preparative HPLC (Chiralpak-AD chiral column) using an isocratic mixture of (EtOH+0.5% formic acid):n-heptane (40:60) gave the desired isomers.

First eluting isomer (example 8): Light yellow solid (44 mg, 17.3%). MS (ESI): m/z=390.11 [M+H]⁺.

Second eluting isomer (example 9): Waxy yellow solid (80 mg, 31.5% yield). MS (ESI): m/z=390.11 [M+H]⁺.

Intermediate 8

4-(Ethoxycarbonyl)-5,6-dihydro-2H-pyran-3-carboxylic acid

A mixture of acetic anhydride (5.19 g, 4.8 mL, 50.9 mmol), DIPEA (6.58 g, 8.89 mL, 50.9 mmol) and sodium formate (5.19 g, 76.3 mmol) was stirred at RT for 1 h. A solution of ethyl 5-(trifluoromethylsulfonyloxy)-3,6-dihydro-2H-pyran-4-carboxylate (8.6 g, 25.4 mmol; prepared according to WO2010038167) in DMF (50 mL) was added dropwise, followed by the addition of palladium (II) acetate (286 mg, 1.27 mmol) and LiCl (3.24 g, 76.3 mmol). After stirring at RT for 1.5 h the black suspension was poured on 2M aqueous HCl solution (100 mL) and EtOAc (100 mL) and the layers were separated. The aqueous layer was extracted twice with EtOAc (100 mL). The organic layers were washed twice with H₂O and once with brine, dried over MgSO₄, filtered, treated with silica gel and evaporated. The compound was purified by silica gel chromatography on a 120 g column using an MPLC system eluting with a gradient of CH₂Cl₂:MeOH (100:0 to 80:20). Light brown oil (4.14 g; 81.3%). MS (ESI): m/z=199.06 [M−H]⁻.

Example 10

(R)-1-[4,5-Dimethyl-3-(3-trifluoromethyl-[1,2,4]oxadiazol-5-yl)-thiophen-2-ylcarbamoyl]-pyrrolidine-2-carboxylic acid

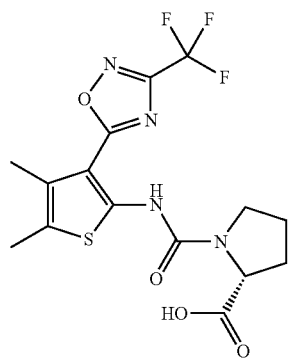 [SMILES: Cc1sc(NC(=O)N2CCC[C@@H]2C(=O)O)c(-c2nc(C(F)(F)F)no2)c1C]

To a solution of 5-(2-isocyanato-4,5-dimethyl-thiophen-3-yl)-3-trifluoromethyl-[1,2,4]-oxadiazole (178 mg, 0.615 mmol) in CH₂Cl₂ (10 mL) were added D-proline (142 mg, 1.23 mmol) and triethylamine (0.128 mL, 0.923 mmol) at 25° C. and the reaction mixture was stirred at 25° C. for 12 h. The reaction mixture was diluted with CH₂Cl₂ (20 mL) and washed with 2N aqueous HCl solution (15 mL) followed by H₂O (20 mL). The organic layer was dried over Na₂SO₄, filtered and evaporated. The residue was purified using silica gel column chromatography using a gradient of CH₂Cl₂:MeOH (100:0 to 95:5) to furnish the desired compound as an off-white solid (120 mg, 48%). MS (ESI): m/z=403.4 (M−H)⁻.

Intermediate 9

5-(2-Isocyanato-4,5-dimethyl-thiophen-3-yl)-3-trifluoromethyl-[1,2,4]-oxadiazole To a solution of 4,5-dimethyl-3-(3-trifluoromethyl-[1,2,4]oxadiazol-5-yl)-thiophen-2-ylamine (165 mg, 0.627 mmol, Int1.22) in THF (4 mL) was added triphosgene (149 mg, 0.501 mmol) and the reaction mixture was stirred at 25° C. for 2 h. The solvent was evaporated to yield the desired compound as a colorless solid (178 mg, 98%) which was used in the next step without purification.

The examples in Table 9 were prepared according to the methods used in example 4, using the 2-aminothiophene and carboxylic acid anhydride reagents as listed in Table 9.

TABLE 9

| No. | Systematic name/Structure | 2-Amino-thiophene | Carboxylic acid anhydride | MS m/z |
|---|---|---|---|---|
| 4.6 | 3-[4,5-Dimethyl-3-(3-methyl-[1,2,4]thiadiazol-5-yl)-thiophen-2-ylcarbamoyl]-bicyclo[2.2.2]oct-2-ene-2-carboxylic acid | 4,5-Dimethyl-3-(3-methyl-[1,2,4]thiadiazol-5-yl)-thiophen-2-ylamine (Int1.20) | Bicyclo[2.2.2]oct-2-ene-2,3-dicarboxylic anhydride (CAS RN 151813-29-5) | 404.2 [M + H]$^+$ |
| 4.7 | 2-[3-(3-Cyclopropyl-[1,2,4]thiadiazol-5-yl)-4,5-dimethyl-thiophen-2-ylcarbamoyl]-cyclopent-1-enecarboxylic acid | 3-(3-Cyclopropyl-[1,2,4]thiadiazol-5-yl)-4,5-dimethyl-thiophen-2-ylamine (Int1.21) | 1-Cyclopentene-1,2-dicarboxylic anhydride (CAS RN 3205-94-5) | 390.0 [M + H]$^+$ |
| 4.8 | 2-[3-(3-Cyclopropyl-[1,2,4]thiadiazol-5-yl)-4,5-dimethyl-thiophen-2-ylcarbamoyl]-cyclohex-1-enecarboxylic acid | 3-(3-Cyclopropyl-[1,2,4]thiadiazol-5-yl)-4,5-dimethyl-thiophen-2-ylamine (Int1.21) | 1-Cyclohexene-1,2-dicarboxylic anhydride (CAS RN 2426-02-0) | 404.2 [M + H]$^+$ |

TABLE 9-continued

| No. | Systematic name/Structure | 2-Amino-thiophene | Carboxylic acid anhydride | MS m/z |
|---|---|---|---|---|
| 4.9 | 3-[3-(3-Cyclopropyl-[1,2,4]thiadiazol-5-yl)-4,5-dimethyl-thiophen-2-ylcarbamoyl]-bicyclo[2.2.2]oct-2-ene-2-carboxylic acid | 3-(3-Cyclopropyl-[1,2,4]thiadiazol-5-yl)-4,5-dimethyl-thiophen-2-ylamine (Int1.21) | Bicyclo[2.2.2]oct-2-ene-2,3-dicarboxylic anhydride (CAS RN 151813-29-5) | 429.8 [M + H]+ |
| 4.10 | 2-[5-Cyclopropyl-4-methyl-3-(3-methyl-[1,2,4]thiadiazol-5-yl)-thiophen-2-ylcarbamoyl]-cyclopent-1-enecarboxylic acid | 5-Cyclopropyl-4-methyl-3-(3-methyl-[1,2,4]thiadiazol-5-yl)-thiophen-2-ylamine (Int1.23) | 1-Cyclopentene-1,2-dicarboxylic anhydride (CAS RN 3205-94-5) | 390.0 [M + H]+ |
| 4.11 | 2-[5-Cyclopropyl-4-methyl-3-(3-methyl-[1,2,4]thiadiazol-5-yl)-thiophen-2-ylcarbamoyl]-cyclohex-1-enecarboxylic acid | 5-Cyclopropyl-4-methyl-3-(3-methyl-[1,2,4]thiadiazol-5-yl)-thiophen-2-ylamine (Int1.23) | 1-Cyclohexene-1,2-dicarboxylic anhydride (CAS RN 2426-02-0) | 404.2 [M + H]+ |

TABLE 9-continued

| No. | Systematic name/Structure | 2-Amino-thiophene | Carboxylic acid anhydride | MS m/z |
|---|---|---|---|---|
| 4.12 | 3-[5-Cyclopropyl-4-methyl-3-(3-methyl-[1,2,4]thiadiazol-5-yl)-thiophen-2-ylcarbamoyl]-bicyclo[2.2.2]oct-2-ene-2-carboxylic acid | 5-Cyclopropyl-4-methyl-3-(3-methyl-[1,2,4]thiadiazol-5-yl)-thiophen-2-ylamine (Int1.23) | Bicyclo[2.2.2]oct-2-ene-2,3-dicarboxylic anhydride (CAS RN 151813-29-5) | 430.0 [M + H]$^+$ |
| 4.13 | 2-[5-Cyclopropyl-3-(3-cyclopropyl-[1,2,4]thiadiazol-5-yl)-4-methyl-thiophen-2-ylcarbamoyl]-cyclopent-1-enecarboxylic acid | 5-Cyclopropyl-3-(3-cyclopropyl-[1,2,4]thiadiazol-5-yl)-4-methyl-thiophen-2-ylamine (Int1.24) | 1-Cyclopentene-1,2-dicarboxylic anhydride (CAS RN 3205-94-5) | 416.0 [M + H]$^+$ |
| 4.14 | 2-[4,5-Dimethyl-3-(3-methyl-[1,2,4]thiadiazol-5-yl)-thiophen-2-ylcarbamoyl]-cyclopent-1-enecarboxylic acid | 4,5-Dimethyl-3-(3-methyl-[1,2,4]thiadiazol-5-yl)-thiophen-2-ylamine (Int1.20) | 1-Cyclopentene-1,2-dicarboxylic anhydride (CAS RN 3205-94-5) | 364.4 [M + H]$^+$ |

TABLE 9-continued

| No. | Systematic name/Structure | 2-Amino-thiophene | Carboxylic acid anhydride | MS m/z |
|---|---|---|---|---|
| 4.15 | 3-[5-Cyclopropyl-3-(3-cyclopropyl-[1,2,4]thiadiazol-5-yl)-4-methyl-thiophen-2-ylcarbamoyl]-bicyclo[2.2.2]oct-2-ene-2-carboxylic acid | 5-Cyclopropyl-3-(3-cyclopropyl-[1,2,4]thiadiazol-5-yl)-4-methyl-thiophen-2-ylamine (Int1.24) | Bicyclo[2.2.2]oct-2-ene-2,3-dicarboxylic anhydride (CAS RN 151813-29-5) | 456.4 [M + H]$^+$ |
| 4.16 | 2-[4,5-Dimethyl-3-(3-methyl-[1,2,4]thiadiazol-5-yl)-thiophen-2-ylcarbamoyl]-cyclohex-1-enecarboxylic acid | 4,5-Dimethyl-3-(3-methyl-[1,2,4]thiadiazol-5-yl)-thiophen-2-ylamine (Int1.20) | 1-Cyclohexene-1,2-dicarboxylic anhydride (CAS RN 2426-02-0) | 378.2 [M + H]$^+$ |
| 4.17 | 2-[5-Cyclopropyl-3-(3-cyclopropyl-[1,2,4]thiadiazol-5-yl)-4-methyl-thiophen-2-ylcarbamoyl]-cyclohex-1-enecarboxylic acid | 5-Cyclopropyl-3-(3-cyclopropyl-[1,2,4]thiadiazol-5-yl)-4-methyl-thiophen-2-ylamine (Int1.24) | 1-Cyclohexene-1,2-dicarboxylic anhydride (CAS RN 2426-02-0) | 430.2 [M + H]$^+$ |

The intermediates in Table 10 were prepared according to methods A7 and A3, respectively as described before and using the starting material as listed in Table 10.

TABLE 10

| No. | Method | Systematic name/ Structure | Starting material(s) | MS m/z |
|---|---|---|---|---|
| Int1.20 | A7 | 4,5-Dimethyl-3-(3-methyl-1,2,4-thiadiazol-5-yl)thiophen-2-amine | Butan-2-one, 2-(3-Methyl-1,2,4-thiadiazol-5-yl)acetonitrile (Int3.4) | 226.2 [M + H]$^+$ |
| Int1.21 | A7 | 3-(3-Cyclopropyl-1,2,4-thiadiazol-5-yl)-4,5-dimethyl-thiophen-2-amine | Butan-2-one, (3-Cyclopropyl-[1,2,4]thiadiazol-5-yl)-acetonitrile (Int3.5) | 252.0 [M + H]$^+$ |
| Int1.22 | A7 | 4,5-Dimethyl-3-[3-(trifluoromethyl)-1,2,4-oxadiazol-5-yl]thiophen-2-amine | Butan-2-one, 2-[3-(Trifluoromethyl)-1,2,4-oxadiazol-5-yl]acetonitrile (Int3.3) | $^1$H-NMR (CDCl$_3$, 400 MHz) δ 6.21 (s, 2H), 2.31 (s, 3H), 2.20 (s, 3H) |
| Int1.23 | A3 | 5-Cyclopropyl-4-methyl-3-(3-methyl-1,2,4-thiadiazol-5-yl)thiophen-2-amine | (E/Z)-3-cyclopropyl-2-(3-methyl-1,2,4-thiadiazol-5-yl)pent-2-enenitrile (Int2.7) | 252.0 [M + H]$^+$ |

TABLE 10-continued

| No. | Method | Systematic name/ Structure | Starting material(s) | MS m/z |
|---|---|---|---|---|
| Int1.24 | A3 | 5-Cyclopropyl-4-methyl-3-(3-methyl-1,2,4-thiadiazol-5-yl)thiophen-2-amine 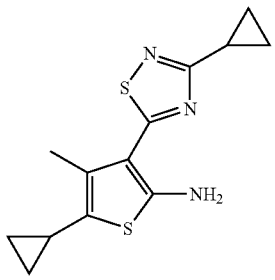 [SMILES: Cc1c(C2CC2)sc(N)c1-c1nc(C2CC2)ns1] | (E/Z)-3-Cyclopropyl-2-(3-cyclopropyl-1,2,4-thiadiazol-5-yl)pent-2-enenitrile (Int2.8) | 278.2 [M + H]+ |

The intermediates in Table 11 were prepared according to method B1 described before and using the starting materials as listed in Table 11:

TABLE 11

| No. | Systematic name/ Structure | Starting material | MS m/z |
|---|---|---|---|
| Int2.7 | (E/Z)-3-cyclopropyl-2-(3-methyl-1,2,4-thiadiazol-5-yl)pent-2-enenitrile 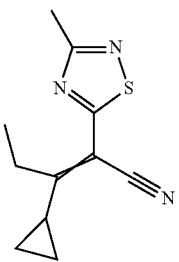 | 1-Cyclopropylpropan-1-one (CAS RN 6704-19-4), 2-(3-Methyl-1,2,4-thiadiazol-5-yl)acetonitrile (Int3.4) | 220.2 [M + H]+ |
| Int2.8 | (E/Z)-3-Cyclopropyl-2-(3-cyclopropyl-1,2,4-thiadiazol-5-yl)pent-2-enenitrile 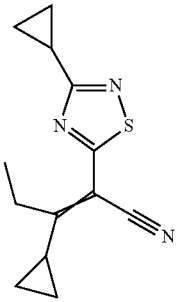 [SMILES: CCC(=C(C#N)c1nc(C2CC2)ns1)C1CC1] | 1-Cyclopropylpropan-1-one (CAS RN 6704-19-4), 2-(3-Cyclopropyl-1,2,4-thiadiazol-5-yl)acetonitrile (Int3.5) | 246.2 [M + H]+ |

General Procedure D: Preparation of Cyanomethyl-Thiadiazoles

To a solution of the 5-chloro-3-alkyl-[1.2.4]thiadiazole (6 mmol) in anhydrous THF (15 mL) is added anhydrous $CH_3CN$ (12 mmol) and the solution is cooled to 0° C. Then LiHMDS (12 mmol, 1M solution in THF) is added dropwise at this temperature and the reaction mixture is stirred at 25° C. for 5 h. The reaction is quenched with saturated aqueous $NH_4Cl$ solution (20 mL) and extracted three times with EtOAc (30 mL each). The combined organic layers are washed with brine, dried over $Na_2SO_4$, filtered and evaporated. The residue is purified by silica gel column chromatography eluting with a gradient of EtOAC:n-heptane to give the desired product which can be used in the next step without further purification.

The intermediates in Table 12 were prepared according to the method described above and using the starting materials as listed in Table 12.

TABLE 12

| No. | Systematic name/ Structure | Starting material(s) | MS m/z |
|---|---|---|---|
| Int3.4 | 2-(3-Methyl-1,2,4-thiadiazol-5-yl)acetonitrile 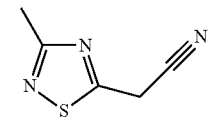 | 5-Chloro-3-methyl-1,2,4-thiadiazole (CAS RN 21734-85-0) | 1H-NMR: (CDCl3, 400 MHz) δ 4.17 (s, 2H), 2.67 (s, 3H) |
| Int3.5 | 2-(3-Cyclopropyl-1,2,4-thiadiazol-5-yl)acetonitrile 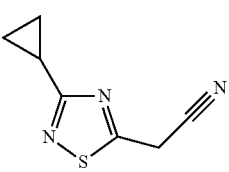 [SMILES: N#CCc1nc(C2CC2)ns1] | 5-Chloro-3-cyclopropyl-1,2,4-thiadiazole (EvoBlocks Ltd.) | 1H-NMR: (CDCl3, 400 MHz) δ 4.12 (s, 2H), 2.34 (q, 1H), 1.05-1.14 (m, 4H) |

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |

-continued

|  | Per tablet |
| --- | --- |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound of formula (I)

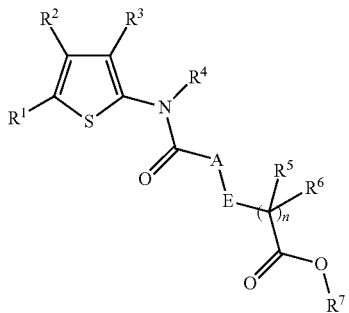

wherein
$R^1$ and $R^2$ are independently selected from H, alkyl, haloalkyl, alkoxyalkyl, haloalkoxyalkyl, cycloalkyl, cycloalkylalkyl, halocycloalkyl, halocycloalkylalkyl, substituted aryl, substituted arylalkyl, substituted heterocycloalkyl, substituted heterocycloalkylalkyl, substituted heteroaryl, substituted heteroarylalkyl, substituted aminocarbonyl, alkoxycarbonyl, haloalkoxycarbonyl and carboxy, wherein substituted aryl, substituted arylalkyl, substituted heterocycloalkyl, substituted heterocycloalkylalkyl, substituted heteroaryl and substituted heteroarylalkyl are substituted with $R^{14}$, $R^{15}$ and $R^{16}$, and wherein substituted aminocarbonyl is substituted on the nitrogen atom with one to two substituents independently selected from H, alkyl, cycloalkyl, haloalkyl, alkylcycloalkyl, cycloalkylalkyl, alkylcycloalkylalkyl, hydroxyalkyl and alkoxyalkyl;
$R^3$ is pyrrolidinyl, substituted [1,2,4]-oxadiazolyl, oxazolyl, substituted thiazolyl, substituted [1,2,4]thiadiazol-5-yl, or pyrimidinyl, wherein substituted [1,2,4]-oxadiazolyl, substituted [1,2,4]thiadiazol-5-yl and substituted thiazolyl are substituted with $R^{17}$;
$R^4$ is H or alkyl;
$R^5$ and $R^6$ are independently selected from H, alkyl and cycloalkyl;
$R^7$ is H, alkyl or cycloalkyl;
A is $NR^8$ or $CR^9R^{10}$;
E is $NR^{11}$ or $CR^{12}R^{13}$;
$R^8$ and $R^{11}$ are independently selected from H, alkyl, haloalkyl, cycloalkyl, halocycloalkyl, cycloalkylalkyl or halocycloalkylalkyl;
$R^9$, $R^{10}$, $R^{12}$ and $R^{13}$ are independently selected from H, halogen, alkyl, haloalkyl or cycloalkyl;
or $R^5$ and $R^{12}$ together with the carbon atoms to which they are attached form a substituted cycloalkyl, substituted cycloalkenyl, substituted aryl, substituted heterocycloalkyl or substituted heteroaryl, wherein substituted cycloalkyl, substituted cycloalkenyl, substituted aryl, substituted heterocycloalkyl and substituted heteroaryl are substituted with $R^{20}$ and can be further substituted with $R^{21}$ and/or $R^{22}$, wherein in case $R^5$ and $R^{12}$ together with the carbon atoms to which they are attached form a substituted aryl or substituted heteroaryl, then $R^6$ and $R^{13}$ are absent;
or $R^8$ and $R^{12}$ together with the nitrogen and carbon atoms to which they are attached form a substituted heterocycloalkyl or substituted heteroaryl, wherein substituted heterocycloalkyl and substituted heteroaryl are substituted with $R^{20}$ and can be further substituted with $R^{21}$ and/or $R^{22}$, wherein in case $R^8$ and $R^{12}$ together with the carbon atoms to which they are attached form a substituted heteroaryl, then $R^{13}$ is absent;
or $R^9$ and $R^{11}$ together with the nitrogen and carbon atoms to which they are attached form a substituted heterocycloalkyl or substituted heteroaryl, wherein substituted heterocycloalkyl and substituted heteroaryl are substituted with $R^{20}$ and can be further substituted with $R^{21}$ and/or $R^{22}$, wherein in case $R^9$ and $R^{11}$ together with the carbon atoms to which they are attached form a substituted heteroaryl, then $R^{10}$ is absent;
or $R^9$ and $R^{12}$ together with the carbon atoms to which they are attached form a substituted cycloalkyl, substituted cycloalkenyl, substituted aryl, substituted heterocycloalkyl or substituted heteroaryl, wherein substituted cycloalkyl, substituted cycloalkenyl, substituted aryl, substituted heterocycloalkyl and substituted heteroaryl are substituted with $R^{20}$ and can be further substituted with $R^{21}$ and/or $R^{22}$, wherein in case $R^9$ and $R^{12}$ together with the carbon atoms to which they are attached form a substituted aryl or substituted heteroaryl, then $R^{10}$ and $R^{13}$ are absent;
or $R^{10}$ and $R^{13}$ together with the carbon atoms to which they are attached form a substituted cycloalkyl, substituted cycloalkenyl, substituted aryl, substituted heterocycloalkyl or substituted heteroaryl, wherein substituted cycloalkyl, substituted cycloalkenyl, substituted aryl, substituted heterocycloalkyl and substituted heteroaryl are substituted with $R^{23}$ and can be further substituted with $R^{24}$ and/or $R^{25}$, wherein in case $R^{10}$ and $R^{13}$ together with the carbon atoms to which they are attached form a substituted aryl or substituted heteroaryl, then $R^9$ and $R^{12}$ are absent;
or $R^{10}$ and $R^{13}$ together with the carbon atoms to which they are attached form a double bond;
$R^{14}$, $R^{15}$, $R^{16}$, $R^{17}$, $R^{20}$, $R^{21}$, $R^{23}$, $R^{24}$ and $R^{25}$ are independently selected from H, hydroxy, oxo, halogen, alkyl, haloalkyl, cycloalkyl, halocycloalkyl, alkoxy, haloalkoxy, alkoxyalkyl, haloalkoxyalkyl, alkoxycarbonyl, carboxy and amino substituted on the nitrogen atom with one to two substituents independently selected from H alkyl, cycloalkyl, haloalkyl, alkylcycloalkyl, cycloalkylalkyl, alkylcycloalkylalkyl, hydroxyalkyl and alkoxyalkyl;

n is zero or 1;

or a pharmaceutically acceptable salt thereof.

2. A compound according to claim 1, wherein $R^1$ is H, alkyl, haloalkyl, cycloalkyl, substituted heterocycloalkyl, substituted heteroaryl, substituted aminocarbonyl and alkoxycarbonyl, wherein substituted heterocycloalkyl and substituted heteroaryl are substituted with $R^{14}$, $R^{15}$ and $R^{16}$, and wherein substituted aminocarbonyl is substituted on the nitrogen atom with two substituents independently selected H, alkyl, cycloalkyl, haloalkyl, alkylcycloalkyl, cycloalkylalkyl, alkylcycloalkylalkyl, hydroxyalkyl and alkoxyalkyl.

3. A compound according to claim 1, wherein $R^2$ is H, alkyl, haloalkyl or cycloalkyl.

4. A compound according to claim 1, wherein $R^3$ is [1,2, 4]-oxadiazolyl substituted with $R^{17}$.

5. A compound according to claim 1, wherein $R^9$ and $R^{12}$ together with the carbon atoms to which they are attached form a substituted cycloalkyl, substituted cycloalkenyl, substituted aryl, substituted heterocycloalkyl or substituted heteroaryl, wherein substituted cycloalkyl, substituted cycloalkenyl, substituted aryl, substituted heterocycloalkyl and substituted heteroaryl are substituted with $R^{20}$ and can be further substituted with $R^{21}$ and/or $R^{22}$, wherein in case $R^9$ and $R^{12}$ together with the carbon atoms to which they are attached form a substituted aryl or substituted heteroaryl, then $R^{10}$ and $R^{13}$ are absent.

6. A compound according to claim 1, wherein $R^{10}$ and $R^{13}$ together with the carbon atoms to which they are attached form a double bond.

7. A compound according to claim 1, wherein $R^{14}$, $R^{15}$, $R^{16}$, $R^{17}$, $R^{18}$, $R^{19}$, $R^{20}$, $R^{21}$, $R^{23}$, $R^{24}$ and $R^{25}$ are independently selected from H, alkyl, haloalkyl and cycloalkyl.

8. A compound according to claim 1, selected from
   5-[(3-Carboxy-bicyclo[2.2.2]oct-2-ene-2-carbonyl)-amino]-3-methyl-4-(4-methyl-thiazol-2-yl)-thiophene-2-carboxylic acid methyl ester;
   2-[4-Cyclopropyl-5-methyl-3-(3-methyl-[1,2,4]oxadiazol-5-yl)-thiophen-2-ylcarbamoyl]-cyclopent-1-enecarboxylic acid;
   3-[4-Cyclopropyl-5-methyl-3-(3-trifluoromethyl-[1,2,4]oxadiazol-5-yl)-thiophen-2-ylcarbamoyl]-bicyclo[2.2.2]oct-2-ene-2-carboxylic acid;
   2-[3-(3-Cyclopropyl-[1,2,4]oxadiazol-5-yl)-4,5-dimethyl-thiophen-2-ylcarbamoyl]-cyclohex-1-enecarboxylic acid;
   2-[5-Cyclopropyl-3-(3-cyclopropyl-[1,2,4]oxadiazol-5-yl)-4-methyl-thiophen-2-ylcarbamoyl]-cyclopent-1-enecarboxylic acid;
   3-[5-Cyclopropyl-3-(3-cyclopropyl-[1,2,4]oxadiazol-5-yl)-4-methyl-thiophen-2-ylcarbamoyl]-bicyclo[2.2.2]oct-2-ene-2-carboxylic acid;
   2-[4-Cyclopropyl-5-methyl-3-(3-methyl-[1,2,4]oxadiazol-5-yl)-thiophen-2-ylcarbamoyl]-cyclohex-1-enecarboxylic acid;
   3-[4-Cyclopropyl-5-methyl-3-(3-methyl-[1,2,4]oxadiazol-5-yl)-thiophen-2-ylcarbamoyl]-bicyclo[2.2.2]oct-2-ene-2-carboxylic acid;
   2-[4-Cyclopropyl-3-(3-cyclopropyl-[1,2,4]oxadiazol-5-yl)-5-methyl-thiophen-2-ylcarbamoyl]-cyclopent-1-enecarboxylic acid;
   3-[4-Cyclopropyl-3-(3-cyclopropyl-[1,2,4]oxadiazol-5-yl)-5-methyl-thiophen-2-ylcarbamoyl]-bicyclo[2.2.2]oct-2-ene-2-carboxylic acid;
   3-[3-(3-Cyclopropyl-[1,2,4]oxadiazol-5-yl)-4,5-dimethyl-thiophen-2-ylcarbamoyl]-bicyclo[2.2.2]oct-2-ene-2-carboxylic acid;
   2-[3-(3-Cyclopropyl-[1,2,4]oxadiazol-5-yl)-4,5-dimethyl-thiophen-2-ylcarbamoyl]-cyclopent-1-enecarboxylic acid;
   2-[4-Cyclopropyl-5-methyl-3-(3-trifluoromethyl-[1,2,4]oxadiazol-5-yl)-thiophen-2-ylcarbamoyl]-cyclopent-1-enecarboxylic acid;
   2-[3-(3-Cyclopropyl-[1,2,4]oxadiazol-5-yl)-5-methyl-thiophen-2-ylcarbamoyl]-cyclopent-1-enecarboxylic acid;
   2-[3-(3-Cyclopropyl-[1,2,4]oxadiazol-5-yl)-thiophen-2-ylcarbamoyl]-cyclopent-1-enecarboxylic acid;
   2-[3-(3-Cyclopropyl-[1,2,4]oxadiazol-5-yl)-4-methyl-5-oxetan-3-yl-thiophen-2-ylcarbamoyl]-cyclopent-1-enecarboxylic acid;
   2-[3-(3-Cyclopropyl-[1,2,4]oxadiazol-5-yl)-4-methyl-5-oxetan-3-yl-thiophen-2-ylcarbamoyl]-cyclohex-1-enecarboxylic acid;
   2-[3-(3-Cyclopropyl-[1,2,4]oxadiazol-5-yl)-5-methyl-4-trifluoromethyl-thiophen-2-ylcarbamoyl]-cyclopent-1-enecarboxylic acid;
   5-[(2-Carboxy-cyclopent-1-enecarbonyl)-amino]-4-(3-cyclopropyl-[1,2,4]oxadiazol-5-yl)-3-methyl-thiophene-2-carboxylic acid ethyl ester;
   2-[3-(3-Cyclopropyl-[1,2,4]oxadiazol-5-yl)-5-dimethylcarbamoyl-4-methyl-thiophen-2-ylcarbamoyl]-cyclopent-1-enecarboxylic acid;
   2-[5-Cyclopropyl-3-(3-cyclopropyl-[1,2,4]oxadiazol-5-yl)-thiophen-2-ylcarbamoyl]-cyclopent-1-enecarboxylic acid;
   2-[4-Cyclopropyl-3-(3-cyclopropyl-[1,2,4]oxadiazol-5-yl)-thiophen-2-ylcarbamoyl]-cyclopent-1-enecarboxylic acid;
   2-[3-(3-Cyclopropyl-[1,2,4]oxadiazol-5-yl)-4-methyl-thiophen-2-ylcarbamoyl]-cyclopent-1-enecarboxylic acid;
   2-[3-(3-Cyclopropyl-[1,2,4]oxadiazol-5-yl)-5-(2,2,2-trifluoro-ethyl)-thiophen-2-ylcarbamoyl]-cyclopent-1-enecarboxylic acid;
   2-[3-(3-Cyclopropyl-[1,2,4]oxadiazol-5-yl)-4-trifluoromethyl-thiophen-2-ylcarbamoyl]-cyclopent-1-enecarboxylic acid; and
   2-[3-(3-Cyclopropyl-[1,2,4]oxadiazol-5-yl)-5-(5-dimethylamino-[1,2,4]thiadiazol-3-yl)-4-methyl-thiophen-2-ylcarbamoyl]-cyclopent-1-enecarboxylic acid;

or a pharmaceutically acceptable salt thereof.

9. A compound according to claim 1, selected from
   3-[4,5-Dimethyl-3-(3-methyl-[1,2,4]thiadiazol-5-yl)-thiophen-2-ylcarbamoyl]-bicyclo[2.2.2]oct-2-ene-2-carboxylic acid;
   2-[3-(3-Cyclopropyl-[1,2,4]thiadiazol-5-yl)-4,5-dimethyl-thiophen-2-ylcarbamoyl]-cyclopent-1-enecarboxylic acid;
   2-[3-(3-Cyclopropyl-[1,2,4]thiadiazol-5-yl)-4,5-dimethyl-thiophen-2-ylcarbamoyl]-cyclohex-1-enecarboxylic acid;
   3-[3-(3-Cyclopropyl-[1,2,4]thiadiazol-5-yl)-4,5-dimethyl-thiophen-2-ylcarbamoyl]-bicyclo[2.2.2]oct-2-ene-2-carboxylic acid;
   2-[5-Cyclopropyl-4-methyl-3-(3-methyl-[1,2,4]thiadiazol-5-yl)-thiophen-2-ylcarbamoyl]-cyclopent-1-enecarboxylic acid;
   2-[5-Cyclopropyl-4-methyl-3-(3-methyl-[1,2,4]thiadiazol-5-yl)-thiophen-2-ylcarbamoyl]-cyclohex-1-enecarboxylic acid;

3-[5-Cyclopropyl-4-methyl-3-(3-methyl-[1,2,4]thiadiazol-5-yl)-thiophen-2-ylcarbamoyl]-bicyclo[2.2.2]oct-2-ene-2-carboxylic acid;

2-[5-Cyclopropyl-3-(3-cyclopropyl-[1,2,4]thiadiazol-5-yl)-4-methyl-thiophen-2-ylcarbamoyl]-cyclopent-1-enecarboxylic acid;

2-[4,5-Dimethyl-3-(3-methyl-[1,2,4]thiadiazol-5-yl)-thiophen-2-ylcarbamoyl]-cyclopent-1-enecarboxylic acid;

3-[5-Cyclopropyl-3-(3-cyclopropyl-[1,2,4]thiadiazol-5-yl)-4-methyl-thiophen-2-ylcarbamoyl]-bicyclo[2.2.2]oct-2-ene-2-carboxylic acid;

(1SR,2SR)-2-[3-(3-Cyclopropyl-[1,2,4]oxadiazol-5-yl)-4,5-dimethyl-thiophen-2-ylcarbamoyl]-cyclohexanecarboxylic acid;

(1RS,2SR)-2-[3-(3-Cyclopropyl-[1,2,4]oxadiazol-5-yl)-4,5-dimethyl-thiophen-2-ylcarbamoyl]-cyclohexanecarboxylic acid;

2-[4,5-Dimethyl-3-(3-methyl-[1,2,4]thiadiazol-5-yl)-thiophen-2-ylcarbamoyl]-cyclohex-1-enecarboxylic acid;

2-[5-Cyclopropyl-3-(3-cyclopropyl-[1,2,4]thiadiazol-5-yl)-4-methyl-thiophen-2-ylcarbamoyl]-cyclohex-1-enecarboxylic acid;

5-[3-(3-Cyclopropyl-[1,2,4]oxadiazol-5-yl)-4,5-dimethyl-thiophen-2-ylcarbamoyl]-3,6-dihydro-2H-pyran-4-carboxylic acid;

4-[3-(3-Cyclopropyl-[1,2,4]oxadiazol-5-yl)-4,5-dimethyl-thiophen-2-ylcarbamoyl]-5,6-dihydro-2H-pyran-3-carboxylic acid; and (R)-1-[4,5-Dimethyl-3-(3-trifluoromethyl-[1,2,4]oxadiazol-5-yl)-thiophen-2-ylcarbamoyl]-pyrrolidine-2-carboxylic acid;

or a pharmaceutically acceptable salt thereof.

10. A compound according to claim 1, selected from

2-[3-(3-Cyclopropyl-[1,2,4]oxadiazol-5-yl)-4,5-dimethyl-thiophen-2-ylcarbamoyl]-cyclohex-1-enecarboxylic acid;

2-[5-Cyclopropyl-3-(3-cyclopropyl-[1,2,4]oxadiazol-5-yl)-4-methyl-thiophen-2-ylcarbamoyl]-cyclopent-1-enecarboxylic acid;

2-[3-(3-Cyclopropyl-[1,2,4]oxadiazol-5-yl)-5-methyl-4-trifluoromethyl-thiophen-2-ylcarbamoyl]-cyclopent-1-enecarboxylic acid; and 2-[4,5-Dimethyl-3-(3-methyl-[1,2,4]thiadiazol-5-yl)-thiophen-2-ylcarbamoyl]-cyclohex-1-enecarboxylic acid;

or a pharmaceutically acceptable salt thereof.

11. A compound according to claim 1, selected from

2-[3-(3-Cyclopropyl-[1,2,4]oxadiazol-5-yl)-4,5-dimethyl-thiophen-2-ylcarbamoyl]-cyclohex-1-enecarboxylic acid;

2-[5-Cyclopropyl-3-(3-cyclopropyl-[1,2,4]oxadiazol-5-yl)-4-methyl-thiophen-2-ylcarbamoyl]-cyclopent-1-enecarboxylic acid; and 2-[3-(3-Cyclopropyl-[1,2,4]oxadiazol-5-yl)-5-methyl-4-trifluoromethyl-thiophen-2-ylcarbamoyl]-cyclopent-1-enecarboxylic acid;

or a pharmaceutically acceptable salt thereof.

12. A process to prepare a compound according to claim 1, comprising the reaction of a compound of formula (II) in the presence of a compound of formula (VI)

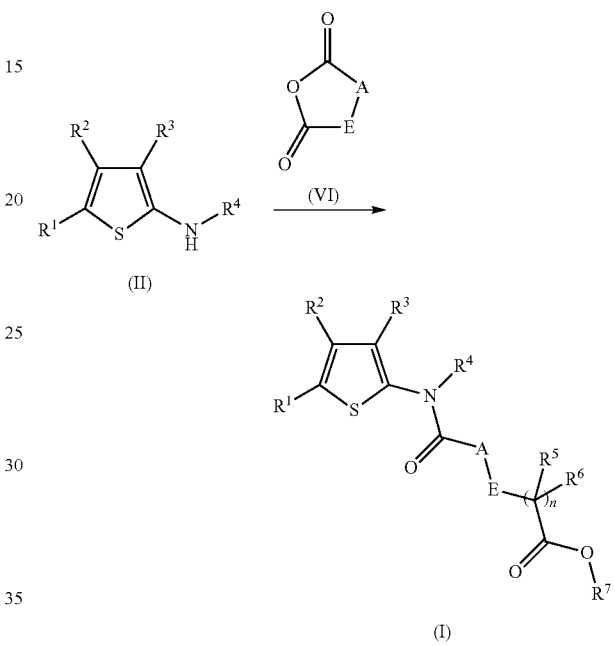

wherein $R^1$, $R^2$, $R^3$, $R^4$, $R^5$, $R^6$, $R^7$ are as defined in claim 1 and wherein n is zero, A is $CR^9R^{10}$ and E is $CR^{12}R^{13}$.

13. A pharmaceutical composition comprising a compound according to claim 1 and a therapeutically inert carrier.

14. A method for the treatment of a condition selected from the group consisting of type 2 diabetes, atherosclerosis, chronic renal disease and non-alcoholic steatohepatitis, which method comprises administering an effective amount of a compound according to claim 1 to a patient in need thereof.

15. A compound manufactured according to a process of claim 12.

* * * * *